US009890197B2

(12) United States Patent
Luyt et al.

(10) Patent No.: US 9,890,197 B2
(45) Date of Patent: Feb. 13, 2018

(54) RHAMM BINDING PEPTIDES

(71) Applicant: The London Health Sciences Centre Research Inc., London (CA)

(72) Inventors: Leonard G. Luyt, London (CA); Eva A. Turley, London (CA); Kenneth Virgel Esguerra, Toronto (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 0 days.

(21) Appl. No.: 14/806,814

(22) Filed: Jul. 23, 2015

(65) Prior Publication Data

US 2016/0031942 A1 Feb. 4, 2016

Related U.S. Application Data

(62) Division of application No. 13/701,240, filed as application No. PCT/CA2011/000613 on May 31, 2011, now Pat. No. 9,090,659.

(60) Provisional application No. 61/349,970, filed on May 31, 2010.

(51) Int. Cl.

| C12Q 1/00 | (2006.01) |
|---|---|
| G01N 33/53 | (2006.01) |
| C12N 5/00 | (2006.01) |
| A61K 49/00 | (2006.01) |
| C07K 7/08 | (2006.01) |
| G01T 1/24 | (2006.01) |
| G01N 33/50 | (2006.01) |
| C07K 14/47 | (2006.01) |
| A61K 51/08 | (2006.01) |
| C07K 7/06 | (2006.01) |
| C07K 14/705 | (2006.01) |
| G01N 33/574 | (2006.01) |
| A61K 38/00 | (2006.01) |

(52) U.S. Cl.
CPC ............ *C07K 7/08* (2013.01); *A61K 49/0043* (2013.01); *A61K 49/0056* (2013.01); *A61K 51/088* (2013.01); *C07K 7/06* (2013.01); *C07K 14/47* (2013.01); *C07K 14/705* (2013.01); *G01N 33/5011* (2013.01); *G01N 33/57492* (2013.01); *G01T 1/249* (2013.01); *A61K 38/00* (2013.01); *G01N 2333/70596* (2013.01)

(58) Field of Classification Search
None
See application file for complete search history.

(56) References Cited

U.S. PATENT DOCUMENTS

| 4,235,871 | A | 11/1980 | Papahadjopoulos et al. |
|---|---|---|---|
| 4,609,893 | A | 9/1986 | Cornish |
| 4,713,325 | A | 12/1987 | Lutz |
| 4,714,681 | A | 12/1987 | Reading |
| 4,716,111 | A | 12/1987 | Osband et al. |
| 4,716,117 | A | 12/1987 | Kuo et al. |
| 4,720,459 | A | 1/1988 | Winkelhake |
| 4,762,915 | A | 8/1988 | Kung et al. |
| 5,824,315 | A | 10/1998 | Nag |
| 6,184,204 | B1 | 2/2001 | Boots et al. |
| 6,271,344 | B1 | 8/2001 | Turley |
| 6,429,291 | B1 | 8/2002 | Turley et al. |
| 6,864,235 | B1 | 3/2005 | Turley et al. |
| 6,911,429 | B2 | 6/2005 | Cruz et al. |
| 7,132,292 | B2 | 11/2006 | Komatsu et al. |
| 8,178,545 | B2 | 10/2012 | Brown |
| 2002/0127227 | A1 | 9/2002 | Holmes et al. |
| 2003/0050236 | A1* | 3/2003 | Dawson ............... A61K 38/08 514/18.9 |
| 2004/0010812 | A1 | 1/2004 | Turley et al. |
| 2005/0009061 | A1 | 1/2005 | Komatsu et al. |
| 2005/0058646 | A1 | 3/2005 | Turley et al. |
| 2006/0148014 | A1 | 7/2006 | Agoulnik et al. |
| 2006/0154312 | A1 | 7/2006 | Agoulnik et al. |
| 2009/0220991 | A1 | 9/2009 | Polakiewicz et al. |
| 2010/0062000 | A1 | 3/2010 | Turley et al. |
| 2010/0281003 | A1 | 11/2010 | Jochim et al. |
| 2010/0290989 | A1 | 11/2010 | Tolg et al. |
| 2013/0157285 | A1 | 6/2013 | Veiseh et al. |

FOREIGN PATENT DOCUMENTS

| WO | 93/21312 A1 | 10/1993 |
|---|---|---|
| WO | 97/24111 A2 | 7/1997 |
| WO | 01/75067 A2 | 10/2001 |

(Continued)

OTHER PUBLICATIONS

Andreu, D., et al., "Chemical Synthesis of Five Tubulin Antigenic Sequences. Production and Characterization of Their Corresponding Anti-Tubulin Monospecific Antibodies," International Journal of Peptide and Protein Research, Jun. 1988, pp. 555-566, vol. 31, No. 6 (Abstract only).

Coe, I. R., et al., "Isolation of Different Brain-Specific Isotypes of Alpha-Tubulins from Chum Salmon (*Oncorhynchus keta*)," DNA Sequence: The Journal of DNA Sequencing and Mapping, 1992, pp. 257-262, vol. 3, No. 4 (Abstract only).

de la Vina, S., et al., "Tubulin Structure Probed with Antibodies to Synthetic Peptides. Mapping of Three Major Types of Limited Proteolysis Fragments," Biochemistry, Jul. 1988, pp. 5352-5365, vol. 27, No. 14 (Abstract only).

Jimenez, M. A., et al., "Helicity of alpha(404-451) and beta(394-445) Tubulin C-Terminal Recombinant Peptides," Protein Science: A Publication of the Protein Society, Apr. 1999, pp. 788-799, vol. 8, No. 4.

(Continued)

*Primary Examiner* — Yong Pak
(74) *Attorney, Agent, or Firm* — Senniger Powers LLP

(57) ABSTRACT

The present invention provides for peptides that bind to Receptor for Hyaluronic Acid Mediated Motility (RHAMM) molecules. More specifically, provided are peptides capable of specifically binding RHAMM molecules and capable of binding RHAMM with substantially high affinity. These novel RHAMM-binding peptides provide the basis for new imaging probes that can be used to identify cells expressing RHAMM, and for methods of imaging, prognosis, diagnosis and treatment of conditions associated with RHAMM expression.

25 Claims, 22 Drawing Sheets

(56) References Cited

FOREIGN PATENT DOCUMENTS

| WO | 2005117876 A1 | 12/2005 |
| --- | --- | --- |
| WO | 2006/063135 A2 | 6/2006 |
| WO | 2006063135 A2 | 6/2006 |
| WO | 2006/086111 A2 | 8/2006 |
| WO | 2007046796 A1 | 4/2007 |
| WO | 2008/138916 A1 | 11/2008 |

OTHER PUBLICATIONS

Mishima, M., et al., "Structural Basis for Tubulin Recognition by Cytoplasmic Linker Protein 170 and Its Autoinhibition," Proceedings of the National Academy of Sciences of the United States of America, Jun. 19, 2007, pp. 10346-10351, vol. 104, No. 25.

Volker, K. W., et al., "A Glycolytic Enzyme Binding Domain on Tubulin," Archives of Biochemistry and Biophysics, Feb. 1997, pp. 237-243, vol. 338, No. 2 (Abstract only).

Assmann, Volker et al, The intracellular hyaluronan receptor RHAMM/IHABP interacts with microtubules and actin filaments, Journal of Cell Science, 1999, p. 3943-3954, 112.

Cowan, N.J. et al, Expression of Human a-Tubulin Genese: Interspecies Conservation of 3' Untranslated Regions, Mole. and Cell. Biol., Oct. 1983, p. 1738-1745, v3.

Cross, Daniel At El, MAP-1 and MAP-2 Binding Sites at the C-Terminus of beta-Tubulin. Studies with Synthetic Tubulin Peptides, Biochemistry, 1991, p. 4362-4366, 30(17).

Edward, M. et al, Tumour regulation of fibroblast hyaluronan expression: a mechanism to facilitate tumour growth and invasion, Carcinogenesis, 2005, p. 1215-1223, 26(7).

Esguerra, Kenneth V. et al, Tubulin derived peptides as optical imaging probes targeting RHAMM, Journal of Nuclear Medicine, 2010, Abstract 394, 51 (Suppl. 2).

Evanko, Stephen P. et al, Intracellular Hyaluronan in Arterial Smooth Muscle Cells: Association with Mircotubules, RHAMM, and the Mitotic Spindle , J. Histochem Cytochem, 2004, p. 1525-1535, 52.

Gotte, Martin and Yip, George W., Heparanase, Hyaluronan, and CD44 in Cancers: A Breast Carcinoma Perspective, Cancer Research, Nov. 2006, p. 10233-10237, 66(21).

Greiner et al., Identification and characterization of epitopes of the receptor for hyaluronic acid-mediated motility (RHAMM/CD168) recognized by CDS+ T cells of HLA-A2-positive patients with acute myeloid leukemia. Blood.106 (3); 938-945. 2005.

Hall, J.L. et al, Identification of Two Human B-Tubulin Isotypes, Mole. and Cell. Biol., May 1983, p. 854-862, 3(5).

U.S. Appl. No. 61/166,211, filed Apr. 2, 2009, 690 pages.

Maxwell et al., Cell-surface and mitotic-spindle RHAMM: moonlighting or dual oncogenic functions?, Journal of Cell Science 121, 2008, 925-932.

Maxwell, Christopher A., et al., Receptor for Hyaluronan-Mediated Motitility Correlates with Centrosome Abnormalities in Multiple Myeloma and Maintains Mitotic Integrity, Cancer Res, 2005, p. 850-860, 65(3).

Maxwell, Christopher At El, RHAMM is a Centrosomal Protein that Interacts with Dyein and Maintains Spindle Pole Stability, Mol. Bio. of the Cell, Jun. 2003, p. 2262-2276, v14.

Pilarski, Linda et al, Potential Role for Hyaluronan and the Hyaluronan Receptor RHAMM in Mobilization and Trafficking of Hematopoietic Progenitor Cells, Blood, May 1999, p. 2918-2927, 93(9).

Savani, R. C., et al., "A Role for Hyaluronan in Macrophage Accumulation and Collagen Deposition after Bleomycin-Induced Lung Injury," American Journal of Respiratory Cell and Molecular Biology, Oct. 2000, pp. 475-484.

Savani, R. C., et al., "Hyaluronan Receptor Antagonists Alter Skin Inflammation and Fibrosis Following Injury," Proceedings of the Western Pharmacology Society, 1995, pp. 131-136, vol. 38.

Sullivan, Kevin and Cleveland, Don W., Identification of conserved isotype-defining variable region sequences for four vertebrate β tubulin polypeptide classes , Prov. Natl. Acad. Sci., Jun. 1986, p. 4327-4331, v83.

Tammi, Markku I. et al, Hyaluronan and Homeostasis: A Balancing Act, Journal of Biological Chemistry, Feb. 2002, 277(7), American Society for Biochemistry and Molecular Biology, Inc., p. 4581-4584.

Tolg, Cornelia et al, RHAMM Promotes Interphase Microtubule Instability and Mitotic Spindle Integrity through MEK1/ERK1/2 Activity, J Biol. Chem., Aug. 2010, p. 26461-26474, 285(34).

Villasante, Alfredo et al, Six Mouse α-Tubulin mRNAs Encode Five Distinct Isotypes: Testis-Specific Expression of Two Sister Genes, Mole. and Cell. Biol., Jul. 1986, p. 2409-2419, 6(7).

Ziebell, M. R., et al., "Peptides that Mimic Glycosaminoglycans: High-Affinity Ligands for a Hyaluronan Binding Domain," Chemistry & Biology, Nov. 2001, pp. 1081-1094, vol. 8, No. 11.

International Search Report and Written Opinion in related PCT/CA2011/000613, dated Oct. 20, 2011, 16 pages.

Ziebell, M. R., et al., "Interactions of Peptide Mimics of Hyaluronic Acid With the Receptor for Hyaluronan Mediated Motility (RHAMM)," Journal of Computer-Aided Molecular Design, 2004, pp. 597-614, vol. 18, No. 10.

Extended European Search Report issued for EP 16185386.6, dated Jun. 26, 2017, 14 pages.

Rudiger, M., et al., "Beta Tubulin of Bull Sperm is Polyglycylated," FEBS Letters, 1995, pp. 147-151, vol. 364, vol. 2.

* cited by examiner

718 LKQKIKHVVKLKDENSQLKSEVSKLRSQLVKRK 750

(SEQ ID. NO. 19)

| Sequence Listing | Peptide | Tubulin Type | Calculated M/Z | Observed M/Z | Purity (%) | $K_D$ (nM) |
|---|---|---|---|---|---|---|
| SEQ ID NO. 1 | 1a | Alpha Ia CTT (440-451) | 678.3 $[M+2H]^{2+}$ | 677.7 $[M+2H]^{2+}$ | 99 | 24 |
| SEQ ID NO. 24 | 1b | | 807.3 $[M+2H]^{2+}$ | 807.6 $[M+2H]^{2+}$ | 98 | |
| SEQ ID NO. 25 | 1c | | 928.8 $[M+2H]^{2+}$ | 927.9 $[M+2H]^{2+}$ | 98 | |
| SEQ ID NO. 2 | 2 | Alpha Ia CTT (438-449) | 658.2 $[M+2H]^{2+}$ | 657.7 $[M+2H]^{2+}$ | 98 | <1000 |
| SEQ ID NO. 3 | 3a | Alpha IIIc CTT (439-450) | 671.3 $[M+2H]^{2+}$ | 670.7 $[M+2H]^{2+}$ | 97 | 331 |
| SEQ ID NO. 26 | 3b | | 800.3 $[M+2H]^{2+}$ | 800.5 $[M+2H]^{2+}$ | 98 | |
| SEQ ID NO. 27 | 3c | | 921.8 $[M+2H]^{2+}$ | 922.1 $[M+2H]^{2+}$ | 98 | |
| SEQ ID NO. 4 | 4 | Alpha IVa CTT (437-448) | 715.2 $[M+2H]^{2+}$ | 714.7 $[M+2H]^{2+}$ | 99 | <1000 |
| SEQ ID NO. 5 | 5 | Alpha VIII CTT (438-449) | 730.8 $[M+2H]^{2+}$ | 730.3 $[M+2H]^{2+}$ | 97 | <1000 |
| SEQ ID NO. 6 | 6 | Alpha Ia H12 (428-439) | 691.8 $[M+2H]^{2+}$ | 691.3 $[M+2H]^{2+}$ | 99 | 330 |
| SEQ ID NO. 7 | 7 | Alpha Ia H12 (416-427) | 653.3 $[M+2H]^{2+}$ | 656.3 $[M+2H]^{2+}$ | 98 | 180 |
| SEQ ID NO. 8 | 8 | Alpha Ia H12 (404-415) | 741.9 $[M+2H]^{2+}$ | 741.3 $[M+2H]^{2+}$ | 99 | 176 |
| SEQ ID NO. 9 | 9a | Beta Ia CTT (433-444) | 692.2 $[M+2H]^{2+}$ | 691.7 $[M+2H]^{2+}$ | 98 | 32 |
| SEQ ID NO. 28 | 9b | | 821.3 $[M+2H]^{2+}$ | 821.7 $[M+2H]2^{+}$ | 99 | |
| SEQ ID NO. 29 | 9c | | 942.8 $[M+2H]^{2+}$ | 943.1 $[M+2H]^{2+}$ | 99 | |

FIG. 2 B

| Sequence Listing | Peptide | Tubulin Type | Calculated M/Z | Observed M/Z | Purity (%) | $K_D$ (nM) |
|---|---|---|---|---|---|---|
| SEQ ID NO. 10 | 10 | Beta IIa CTT (434-445) | 685.2 $[M+2H]^{2+}$ | 684.7 $[M+2H]^{2+}$ | 98 | <1000 |
| SEQ ID NO. 11 | 11a | Beta IVa CTT (433-444) | 684.3 $[M+2H]^{2+}$ | 683.8 $[M+2H]^{2+}$ | 97 | 130 |
| SEQ ID NO. 30 | 11b | | 813.3 $[M+2H]^{2+}$ | 813.6 $M+2H]^{2+}$ | 97 | |
| SEQ ID NO. 31 | 11c | | 934.8 $[M+2H]^{2+}$ | 935.1 $M+2H]^{2+}$ | 96 | |
| SEQ ID NO. 12 | 12a | Beta VI CTT (435-446) | 706.3 $[M+2H]^{2+}$ | 705.8 $[M+2H]^{2+}$ | 99 | 211 |
| SEQ ID NO. 32 | 12b | | 835.3 $[M+2H]^{2+}$ | 835.6 $M+2H]^{2+}$ | 99 | |
| SEQ ID NO. 33 | 12c | | 956.8 $[M+2H]^{2+}$ | 957.1 $M+2H]^{2+}$ | 98 | |
| SEQ ID NO. 13 | 13 | Beta IIIa H12 (413-424) | 714.4 $[M+2H]^{2+}$ | 713.8 $[M+2H]^{2+}$ | 99 | <1000 |
| SEQ ID NO. 14 | 14a | Beta IIIa H12 (408-419) | 685.2 $[M+2H]^{2+}$ | 684.8 $[M+2H]^{2+}$ | 99 | 30 |
| SEQ ID NO. 34 | 14b | | 814.4 $[M+2H]^{2+}$ | 813.8 $[M+2H]^{2+}$ | 98 | |
| SEQ ID NO. 35 | 14c | | 935.8 $[M+2H]^{2+}$ | 936.1 $[M+2H]^{2+}$ | 97 | |
| SEQ ID NO. 15 | 15 | Gamma I CTT (440-451) | 740.4 $[M+2H]^{2+}$ | 740.4 $[M+2H]^{2+}$ | 98 | <1000 |
| SEQ ID NO. 16 | 16 | Gamma I H12 (428-439) | 693.2 $[M+2H]^{2+}$ | 693.8 $[M+2H]^{2+}$ | 95 | <1000 |
| SEQ ID NO. 17 | 17 | Gamma I H12 (416-427) | 711.4 $[M+2H]^{2+}$ | 711.3 $[M+2H]^{2+}$ | 99 | <1000 |

FIG. 2 C

| Buffer PH | RHAMM Concentration (µg/mL) | Ligand Density (RU) |
|---|---|---|
| 10.1 | 30 | 1445.1 ± 31.4 |
| 9.7 | 30 | 1547.8 ± 29.0 |
| 9.1 | 30 | 1499.5 ± 34.4 |
| 7.0 | 30 | 1475.4 ± 13.7 |
| 9.7 | 0 | 27.22 ± 3.57 |
FIG. 3 A
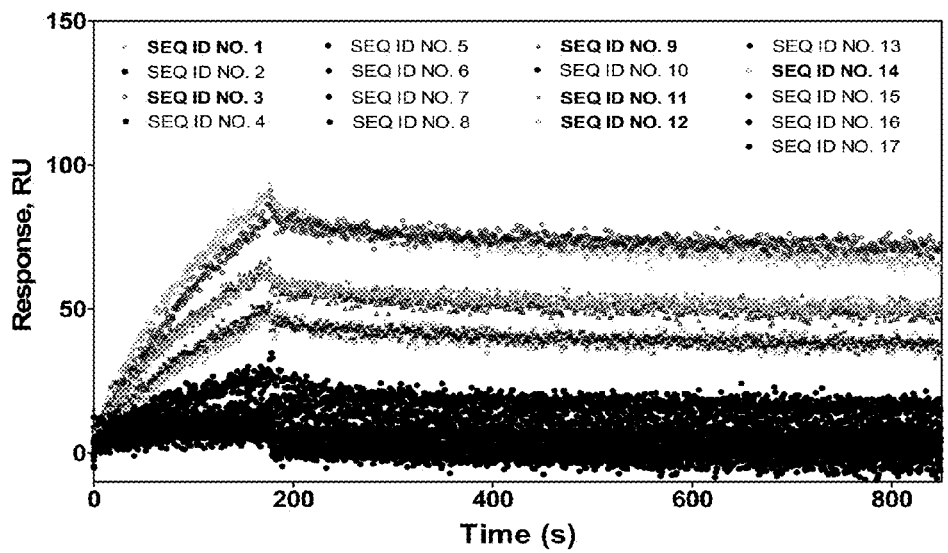
FIG. 3 B
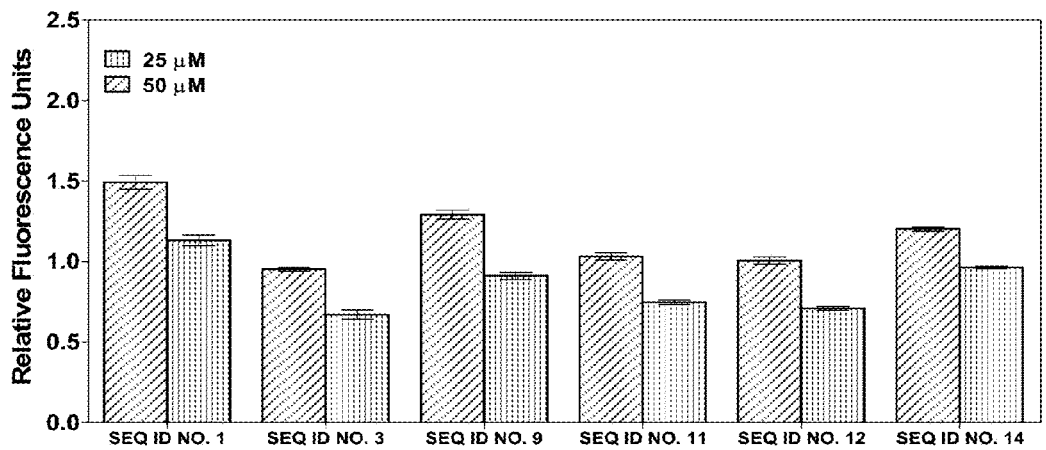
FIG. 3 C

| Sequence | [Conc.] (nM) | $K_{ON}$ ($nM^{-1}$ $sec^{-1}$) | $K_{OFF}$ ($sec^{-1}$) ($10^{-3}$) | $K_D$ (nM) | Ave. $K_D$ (nM) |
|---|---|---|---|---|---|
| SEQ ID NO. 3 | 1000 | 1404 | 0.502 | 358.2 | 331.1 ± 24.5 |
|  | 750 | 1594 | 0.517 | 324.6 |  |
|  | 500 | 1620 | 0.503 | 310.4 |  |
| SEQ ID NO. 11 | 1000 | 855 | 0.102 | 119.8 | 130 ± 12.9 |
|  | 750 | 1189 | 0.172 | 144.7 |  |
|  | 500 | 1485 | 0.187 | 126.0 |  |
| SEQ ID NO. 1 | 1000 | 5046 | 0.124 | 24.5 | 24.2 ± 0.4 |
|  | 750 | 9371 | 0.224 | 23.8 |  |
|  | 500 | 9436 | 0.234 | 24.4 |  |
| SEQ ID NO. 9 | 1000 | 5347 | 0.173 | 32.4 | 32.6 ± 1.1 |
|  | 750 | 5808 | 0.196 | 33.8 |  |
|  | 500 | 7014 | 0.222 | 31.7 |  |
| SEQ ID NO. 12 | 1000 | 1090 | 0.219 | 201.4 | 211.3 ± 8.6 |
|  | 750 | 1101 | 0.237 | 215.4 |  |
|  | 500 | 1594 | 0.346 | 217.0 |  |
| SEQ ID NO. 14 | 1000 | 3202 | 0.10 | 31.9 | 30.2 ± 1.5 |
|  | 750 | 4033 | 0.11 | 29.0 |  |
|  | 500 | 4189 | 0.12 | 29.6 |  |
| RHAMM mAb | 1000 | 37484 | 0.22 | 5.96 | 5.53 ± 0.4 |
|  | 750 | 42913 | 0.23 | 5.45 |  |
|  | 500 | 45172 | 0.23 | 5.18 |  |

SEQ ID NO. 19

FIG. 8B

| | | | | | | | | | | | | | |
|---|---|---|---|---|---|---|---|---|---|---|---|---|---|
| SEQ ID NO. 1 | V | E | G | E | G | E | E | E | G | E | E | Y | |
| SEQ ID NO. 3 | S | V | E | A | E | A | E | E | G | E | E | Y | |
| SEQ ID NO. 9 | | E | E | D | F | G | E | E | A | E | E | E | A |
| SEQ ID NO. 11 | | | G | E | F | E | E | E | A | E | E | E | V | A |

SEQUENCE LISTING

```
<160> NUMBER OF SEQ ID NOS: 58

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Glu Gly Glu Gly Glu Glu Glu Gly Glu Glu Tyr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ser Ala Asp Gly Glu Asp Glu Gly Glu Glu Tyr
1               5                   10

<210> SEQ ID NO 3
<211> LENGTH: 12
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 3

Ser Val Glu Ala Glu Ala Glu Glu Gly Glu Glu Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Asp Ser Tyr Glu Asp Glu Asp Glu Gly Glu Glu
1               5                   10

<210> SEQ ID NO 5
<211> LENGTH: 12
<212> TYPE: PRT
<213> ORGANISM: Artificial sequence
<220> FEATURE:
<223> OTHER INFORMATION: Description of Artificial Sequence: Synthetic
      peptide

<400> SEQUENCE: 5

Asp Ser Phe Glu Glu Glu Asn Glu Gly Glu Glu Phe
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu Lys Asp Tyr Glu Glu Val Gly Val Asp Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Glu Phe Ser Glu Ala Arg Glu Asp Met Ala Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Val His Trp Tyr Val Gly Glu Gly Met Glu Glu
1               5                   10
```

```
<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Glu Asp Phe Gly Glu Glu Ala Glu Glu Glu Ala
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Phe Glu Glu Glu Glu Gly Glu Asp Glu Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Glu Phe Glu Glu Glu Ala Glu Glu Glu Val Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ala Phe Glu Asp Glu Glu Glu Glu Ile Asp Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Asn Met Asn Asp Leu Val Ser Glu Tyr Gln Gln
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Phe Thr Glu Ala Glu Ser Asn Met Asn Asp Leu Val
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Pro Asp Tyr Ile Ser Trp Gly Thr Gln Glu Gln
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Gln Gln Leu Ile Asp Glu Tyr His Ala Ala Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Asn Pro Asp Glu Met Asp Thr Ser Arg Glu Ile
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (6)..(6)
<223> OTHER INFORMATION: Tyr or Glu

<400> SEQUENCE: 18

Glu Glu Xaa Glu Glu Xaa
1               5

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

```
Leu Lys Gln Lys Ile Lys His Val Val Lys Leu Lys Asp Glu Asn Ser
1               5                   10                  15

Gln Leu Lys Ser Glu Val Ser Lys Leu Arg Ser Gln Leu Val Lys Arg
            20                  25                  30

Lys

<210> SEQ ID NO 20
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Arg Asp Ser Tyr Ala Gln Leu Leu Gly His Gln Asn Leu Lys Gln Lys
1               5                   10                  15

Ile Lys His Val Val Lys Leu Lys Asp Glu Asn Ser Gln Leu Lys Ser
            20                  25                  30

Glu Val Ser Lys Leu Arg Ser Gln Leu Val Lys Arg Lys Gln Asn Glu
        35                  40                  45

Leu Arg Leu Gln Gly Glu Leu Asp Lys Ala Leu Gly Ile
    50                  55                  60

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Glu Gly Glu Glu
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala of Gly
<220> FEATURE:
<221> NAME/KEY: MOD_RES
<222> LOCATION: (6)..(6)
<223> OTHER INFORMATION: Tyr or Glu

<400> SEQUENCE: 22

Asp Glu Xaa Glu Glu Xaa
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Ala or Gly
<220> FEATURE:
<221> NAME/KEY: MOD_RES
<222> LOCATION: (6)..(6)
<223> OTHER INFORMATION: Tyr or Glu

<400> SEQUENCE: 23

Glu Glu Xaa Glu Asp Xaa
1               5

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
<223> OTHER INFORMATION: Ahx

<400> SEQUENCE: 24

Cys Xaa Val Glu Gly Glu Gly Glu Glu Glu Gly Glu Glu Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 25

Xaa Val Glu Gly Glu Gly Glu Glu Glu Gly Glu Glu Tyr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
<223> OTHER INFORMATION: Ahx

<400> SEQUENCE: 26

Cys Xaa Ser Val Glu Ala Glu Ala Glu Glu Gly Glu Glu Tyr
1               5                   10

<210> SEQ ID NO 27
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 27

Xaa Ser Val Glu Ala Glu Ala Glu Glu Gly Glu Glu Tyr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
<223> OTHER INFORMATION: Ahx

<400> SEQUENCE: 28

Cys Xaa Glu Glu Asp Phe Gly Glu Glu Ala Glu Glu Glu Ala
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 29

Xaa Glu Glu Asp Phe Gly Glu Glu Ala Glu Glu Glu Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
```

<223> OTHER INFORMATION: Ahx

<400> SEQUENCE: 30

Cys Xaa Gly Glu Phe Glu Glu Glu Ala Glu Glu Glu Val Ala
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 31

Xaa Gly Glu Phe Glu Glu Glu Ala Glu Glu Glu Val Ala
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
<223> OTHER INFORMATION: Ahx

<400> SEQUENCE: 32

Cys Xaa Glu Ala Phe Glu Asp Glu Glu Glu Glu Ile Asp Gly
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 33

Xaa Glu Ala Phe Glu Asp Glu Glu Glu Glu Ile Asp Gly
1               5                   10

<210> SEQ ID NO 34
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Cys
<220> FEATURE:
<221> NAME/KEY: MOD_RES
<222> LOCATION: (2)..(2)
<223> OTHER INFORMATION: Ahx

<400> SEQUENCE: 34

Cys Xaa Phe Thr Glu Ala Glu Ser Asn Met Asn Asp Leu Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Ahx
<220> FEATURE:
<221> NAME/KEY: MOD_RES
<222> LOCATION: (1)..(1)
<223> OTHER INFORMATION: Ahx

<400> SEQUENCE: 35

Xaa Phe Thr Glu Ala Glu Ser Asn Met Asn Asp Leu Val
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Glu Gly Glu Gly Glu Glu Glu Gly Glu Glu Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ala Gly Glu Gly Glu Glu Glu Gly Glu Glu Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Glu Ala Glu Gly Glu Glu Glu Gly Glu Glu Tyr
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Glu Gly Ala Gly Glu Glu Gly Glu Glu Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Glu Gly Glu Ala Glu Glu Gly Glu Glu Tyr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Glu Gly Glu Gly Ala Glu Glu Gly Glu Glu Tyr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Glu Gly Glu Gly Glu Ala Glu Glu Gly Glu Glu Tyr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Glu Gly Glu Gly Glu Glu Ala Gly Glu Glu Tyr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Val Glu Gly Glu Gly Glu Glu Glu Ala Glu Glu Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Glu Gly Glu Gly Glu Glu Glu Gly Ala Glu Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Glu Gly Glu Gly Glu Glu Glu Gly Glu Ala Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Val Glu Gly Glu Gly Glu Glu Glu Gly Glu Glu Ala
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Thr Glu Ala Glu Ser Asn Met Asn Asp Leu Ala
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Thr Glu Ala Glu Ser Asn Met Asn Asp Ala Val
1               5                   10

<210> SEQ ID NO 50
<211> LENGTH: 12
```

```
<212> TYPE: PRT
<213> ORGANISM: Artificial Sequnce
<220> FEATURE:
<223> OTHER INFORMATION: Description of Artificial Sequence: Synthetic
      peptide

<400> SEQUENCE: 50

Phe Thr Glu Ala Glu Ser Asn Met Asn Ala Leu Val
1               5                   10

<210> SEQ ID NO 51
<211> LENGTH: 12
<212> TYPE: PRT
<213> ORGANISM: Artificial Sequnce
<220> FEATURE:
<223> OTHER INFORMATION: Description of Artificial Sequence: Synthetic
      peptide

<400> SEQUENCE: 51

Phe Thr Glu Ala Glu Ser Asn Met Ala Asp Leu Val
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Thr Glu Ala Glu Ser Ala Met Asn Asp Leu Val
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Thr Glu Ala Glu Ser Met Asn Asp Leu Val
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Phe Thr Glu Ala Glu Ala Asn Met Asn Asp Leu Val
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Thr Glu Ala Ala Ser Asn Met Asn Asp Leu Val
```

```
<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Thr Ala Ala Glu Ser Asn Met Asn Asp Leu Val
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Phe Ala Glu Ala Glu Ser Asn Met Asn Asp Leu Val
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Thr Glu Ala Glu Ser Asn Met Asn Asp Leu Val
1               5                   10
```

US 9,890,197 B2

RHAMM BINDING PEPTIDES

CROSS-REFERENCE TO RELATED APPLICATIONS

This application is a divisional of U.S. patent application Ser. No. 13/701,240, filed on Nov. 30, 2012, which is a U.S. PCT National Patent Application of PCT/CA2011/000613, filed May 31, 2011, which claims priority to U.S. Provisional Application No. 61/349,970, filed on May 31, 2010. Each of the above-cited applications is incorporated in its entirety herein by reference.

FIELD OF THE INVENTION

The present invention relates to novel peptides and their use in compositions and methods for identifying cells expressing RHAMM, and in compositions and methods of treatment of disorders or conditions that result from the formation of RHAMM/ligand complex.

BACKGROUND OF THE INVENTION

Throughout this application, various references are cited in square brackets to describe more fully the state of the art to which this invention pertains.

Hyaluronan (HA, an anionic polymer of repeating units of glucuronic acid and N-acetylglucosamine) is one extracellular matrix (ECM) component of stroma, that is associated with cancer progression: increased accumulation of tumor HA is prognostic of poor outcome in cancer patients [1, 2, 3]. HA stimulates cancer cell motility in vitro, suggesting its importance in cancer cell invasion in vivo. Two HA cellular receptors that have been implicated in cancer progression are CD44 and RHAMM (receptor for HA-mediated motility).

Progenitor or "tumour initiating cells" are now generally accepted to disproportionately contribute to the tumour forming potential of leukemias. A similar phenomenon has more recently been described in breast cancer (BC) and other solid tumours and the phenotype of these tumour cell subsets has been partially characterized as CD44+/CD24−/ESA+. Although the precise relationship of these cell subsets to clinical outcome is controversial, CD44+ cells sorted by FACS from primary BC express a gene signature that predicts poor clinical outcome. RHAMM mRNA and protein hyper-expression also occur in primary human breast tumour cell subsets and the presence of these RHAMM positive subsets is predictive of poor clinical outcome and increased risk of peripheral metastasis in BC. Although CD44 is expressed in many normal tissues, RHAMM expression is not detected in these tissues but appears following wound repair and during pathological processes such as cancer progression. Imaging of CD44-positive and RHAMM-positive tumour cell subsets would therefore be relevant in identifying patients at risk for poor outcome. However, as to the date of this document these and/or other tumour progenitor cells have not yet been directly imaged. It would, therefore, be advantageous to find a molecular imaging probe capable of targeting RHAMM to provide a means of imaging progenitor cell status non-invasively. This targeting method could also provide a method of selectively targeting progenitor cells with a therapeutic drug agent, either directly through the ligand-receptor interaction, or indirectly by delivering a therapeutic payload to the targeted cells. For example, one could deliver particle emitting isotopes to the progenitor cells, or could deliver a chemotherapeutic to the cells (eg. Cisplatin). The present invention provides for novel peptide ligands for targeting RHAMM, which has not been previously reported.

SUMMARY OF THE INVENTION

The present invention relates to the discovery of novel peptides that are capable of binding to RHAMM.

Thus in one embodiment, the present invention provides for an isolated peptide comprising at least one amino acid sequence selected from the group comprising at least the following amino acid sequences: SEQ ID NO: 1 to SEQ ID NO: 17.

In another aspect, the present invention provides for an isolated DNA, said DNA comprising a nucleic sequence encoding peptides according to SEQ. ID No. 1 to SEQ ID NO: 17.

The present invention also relates to the discovery of peptides binding with specificity and affinity to a RHAMM, wherein said peptides are derived from tubulin. In one aspect the RHAMM-binding peptides of the present invention are derived from the carboxy terminal tails of tubulin.

According to one embodiment, the present invention provides for a RHAMM-binding peptide, wherein said RHAMM-binding peptide comprises at least one amino acid sequence selected from the group consisting of SEQ ID NO: 1 to SEQ ID NO: 17.

According to another embodiment, the present invention provides for a RHAMM-binding peptide characterized in that said RHAMM-binding peptide comprises a sequence having a formula EEXEEZ (SEQ ID NO: 18), wherein X is selected from alanine or glycine, and Z is selected from tyrosine or glutamic acid.

In another embodiment, the present invention provides for a pharmaceutical composition characterized in that said pharmaceutical composition comprises an effective amount of one or more of the RHAMM-binding peptides of the present invention and a pharmaceutically acceptable carrier.

In another embodiment, the present invention provides for a probe comprising a RHAMM-binding peptide of the present invention and a detectable label capable of being detected by a detection technique.

In one embodiment, the present invention provides for a method of imaging RHAMM expression in tissues or organs of a subject, characterized in that the method comprises: (a) administering a probe comprising a RHAMM-binding peptide of the present invention and a detectable label capable of being detected by a detection technique; and (b) applying the imaging technique for detecting the label in the tissues or organs of the subject.

In another embodiment a method of determining the presence of RHAMM in cells is provided, characterized in that said method comprises contacting cells with a probe comprising a RHAMM-binding peptide of the present invention and a detectable label capable of being detected by a detection technique, and applying the imaging technique for detecting the label in the cells, wherein a detection of labels in the cells indicates the presence of RHAMM in the cells.

In one embodiment, the present invention provides for a method of imaging tumor progenitor cells in a subject characterized in that said method comprises administering a probe comprising a RHAMM-binding peptide of the present invention and a detectable label capable of being detected by a detection technique to the subject and applying the imaging technique for detecting the label in the subject, wherein a detection of labels in the subject indicates the presence of tumor progenitor cells in the subject.

In another embodiment, the present invention is a method of imaging tumor progenitor cells in animal cells, tissues or organs characterized in that said method comprises contacting the cells, tissues or organs with a probe comprising a RHAMM-binding peptide of the present invention and a detectable label capable of being detected by a detection technique, and applying the imaging technique for detecting the label in the cells, tissues or organs, wherein a detection of labels in the cells, tissues or organs indicates the presence of tumor progenitor cells in the cells, tissues or organs.

In one embodiment the present invention provides for a method for determining a prognosis for a cancer patient characterized in that said method comprises: (a) obtaining a tumor tissue sample from the patient; (b) contacting said sample with a probe comprising a RHAMM-binding peptide of the present invention and a detectable label capable of being detected by a detection technique; (c) applying the imaging technique for detecting the label in the sample; and (d) determining the prognosis of the patient, wherein the prognosis predicts a probability of aggressiveness or metastasis of the cancer in the patient, and wherein the detection of RHAMM expression in the sample indicates a poor prognosis.

In another embodiment, the present invention provides for a method for determining a course of treatment for a cancer patient characterized in that the method comprises: (a) obtaining a tumor tissue sample from the patient; (b) contacting said sample with a probe comprising a RHAMM-binding peptide of the present invention and a detectable label capable of being detected by a detection technique; (c) applying the imaging technique for detecting the label in the sample; and (d) determining the prognosis of the patient, wherein the prognosis predicts a probability of aggressiveness of the cancer in the patient, and wherein the detection of RHAMM expression in the sample indicates a poor prognosis; and prescribing a course of treatment for the patient based on the prognosis.

In another embodiment, the present invention provides for a method for diagnosing a patient of a disorder or condition associated with RHAMM expression in cells characterized in that said method comprises: (a) obtaining a tissue sample from the patient; (b) contacting said sample with a probe comprising a RHAMM-binding peptide of the present invention and a detectable label capable of being detected by a detection technique; and (c) applying the imagining technique for detecting the label in the sample; wherein detection of RHAMM expression in the sample indicates a positive diagnosis of the disorder or condition.

In one embodiment, the present invention provides for a method for treating a subject suffering from a disorder or condition associated with RHAMM expression in cells characterized in that said method comprises administering to the subject an effective amount of a composition comprising an effective amount of one or more RHAMM-binding peptides or nucleic acids molecules encoding said one or more RHAMM-binding peptides and a pharmaceutically acceptable carrier, wherein said one or more RHAMM-binding peptides comprise a sequence having a formula EEXEEZ (SEQ ID NO: 18), wherein X is selected from alanine or glycine, and Z is selected from tyrosine or glutamic acid.

In one embodiment, the present invention provides for a method for treating a subject suffering from a disorder or condition associated with RHAMM expression in cells characterized in that said method comprises administering to the subject an effective amount of a composition comprising an effective amount of one or more RHAMM-binding peptides or nucleic acids molecules encoding said one or more RHAMM-binding peptides and a pharmaceutically acceptable carrier, wherein said one or more RHAMM-binding peptides is or are selected from the group consisting of SEQ ID NOs. 1-17.

In another embodiment, the present invention provides for a method of inhibiting proliferation of cells expressing RHAMM characterized in that said method comprises contacting the cells with an effective amount of one or more RHAMM-binding peptides or nucleic acids molecules encoding said one or more RHAMM-binding peptides, wherein said one or more RHAMM-binding peptides comprise a sequence having a formula EEXEEZ (SEQ ID NO: 18), wherein X is selected from alanine or glycine, and Z is selected from tyrosine or glutamic acid.

In another embodiment, the present invention provides for a method of inhibiting proliferation of cells expressing RHAMM characterized in that said method comprises contacting cells with an effective amount one or more RHAMM-binding peptides or nucleic acids molecules encoding said one or more RHAMM-binding peptides, wherein said one or more RHAMM-binding peptides is or are selected from the group consisting of SEQ ID NOs. 1-17.

In another embodiment, the present invention provides for a method of inhibiting the motility of cells expressing RHAMM characterized in that said method comprises contacting the cells with an effective of one or more RHAMM-binding peptides or nucleic acids molecules encoding said one or more RHAMM-binding peptides, wherein said one or more RHAMM-binding peptides comprise a sequence having a formula EEXEEZ (SEQ ID NO: 18), wherein X is selected from alanine or glycine, and Z is selected from tyrosine or glutamic acid.

In another embodiment, the present invention provides for a method of inhibiting the motility of cells expressing RHAMM characterized in that said method comprises contacting the cells with an effective amount of one or more RHAMM-binding peptides or nucleic acids molecules encoding said one or more RHAMM-binding peptides, wherein said one or more RHAMM-binding peptides is or are selected from the group consisting of SEQ ID NOs. 1-17.

In aspects of the invention said cells expressing RHAMM are cancer cells.

In one embodiment, the present invention provides for a method of preventing metastasis in a patient having cancer characterized in that said method comprises administering to the patient an effective amount of a composition comprising one or more RHAMM-binding peptides or nucleic acids molecules encoding said one or more RHAMM-binding peptides, wherein said one or more RHAMM-binding peptides comprise a sequence having a formula EEXEEZ (SEQ ID NO: 18), wherein X is selected from alanine or glycine, and Z is selected from tyrosine or glutamic acid.

In another embodiment, the present invention provides for a method of preventing metastasis in a patient having cancer characterized in that said method comprises administering to the patient an effective amount of a composition comprising one or more RHAMM-binding peptides or nucleic acids molecules encoding said one or more RHAMM-binding peptides, wherein said one or more RHAMM-binding peptides is or are selected from the group consisting of SEQ ID NOs. 1-17.

In one embodiment the present invention provides for a use of a RHAMM-binding peptide in the treatment, amelioration or prevention of a disorder or condition associated with RHAMM expression characterized in that said RHAMM-binding peptide comprises a sequence having a formula EEXEEZ (SEQ ID NO: 18), wherein X is selected from alanine or glycine, and Z is selected from tyrosine or glutamic acid.

In another embodiment the present invention provides for a use of a RHAMM-binding peptide or nucleic acid coding for said RHAMM-binding peptide in the treatment, amelioration or prevention of a disorder or condition associated with RHAMM expression, characterized in that said RHAMM-binding peptide is selected from the group consisting of SEQ ID NOs: 1-17.

In aspects of the invention the disorder or condition associated with RHAMM expression is tissue scarring. In aspects of the invention the disorder or condition associated with RHAMM expression is cancer.

In aspects of the invention, the peptides of the invention may have added: cysteines to one or both ends of the peptide to cyclize by means of disulfide bond formation, phosphorous groups and acetyl groups.

Also within the scope of the invention are functional analogues of any of the peptides of the invention as well as multimers of the peptides according to the invention such as for example a dimer or trimer of the peptides according to the invention. A multimer according to the invention can either be a homomer, consisting of a multitude of the same peptide, or a heteromer consisting of different peptides. The characteristic amino acid sequences of the peptides according to the invention can be flanked by random amino acid sequences. Preferred are flanking sequences that have a stabilizing effect on the peptides, thus increasing their biological availability. Flanking sequences may also be used to improve pharmacokinetic behaviour. Also within the scope of the invention are fusion peptides and pegylated peptides that can improve metabolic stability, increase bioavailability, lower susceptibility to proteolysis.

Also within the scope of the invention are peptides characterized by at least one amino acid being replaced by another amino acid with similar chemical properties; at least one amino acid being replaced by an unnatural amino acid, such as an N-methylated amino acid, D-amino acid, or other unnatural amino acid construct; at least one additional amino acid being present at the N- or/and C-terminus; at least one amino acid being deleted; and at least one amino acid being chemically modified.

BRIEF DESCRIPTION OF THE DRAWINGS

The present invention will become more fully understood from the detailed description given herein and from the accompanying drawings, which are given by way of illustration only and do not limit the intended scope of the invention.

FIG. 1 B illustrates a flow chart of molecular imaging probe design and optimization.

FIGS. 2 B and 2 C provide a table of 17 synthesized tubulin-derived peptides, including peptides derivatized with fluorescein or N-acetyl cysteine, tubulin fragment type, calculated and observed mass spectrometry m/z values (m is representative of molecular or atomic mass and z is representative of the number of elementary charges carried by the ion), percent purity and binding constant Kd. FIGS. 2 B and 2 C disclose SEQ ID NOs: 1, 24-25, 2-3, 26-27, 4-9, 28-29, 10-11, 30-31, 12, 32-33, 13-14, 34-35 and 15-17, respectively, in order of appearance.

FIG. 3 A is a table illustrating pH dependence of RHAMM-CT immobilization to a surface plasmon resonance (SPR) sensor plate. Ligand density was determined from the average SPR response of six measurements. With RHAMM pI=10.1, sodium bicarbonate buffer (pH 9.7) for control run was used. Proteins were coupled to the sensor plate using EDAC (100 mM) and sulfo-NHS (25 mM).

FIG. 3 B illustrates surface plasmon resonance (SPR)-based screening of purified tubulin-derived peptides (SEQ ID NOs: 1-17) against RHAMM to determine high affinity ligands. Screening resulted in six high affinity ligands (SEQ ID NOs: 1, 3, 9, 11, 12 and 14) for RHAMM.

FIG. 3 C is an ELISA binding assay to verify the affinity of six peptides (SEQ ID NOs: 1, 3, 9, 11, 12 and 14) after SPR-screening illustrating the binding of fluorescein-labelled peptides of the present invention to RHAMM. Negative control (no immobilized RHAMM) was subtracted for each of the measurements.

FIG. 4 B is a table illustrating the kinetic profile of selected tubulin-derived peptides (SEQ ID NOs: 1, 3, 9, 11, 12 and 14) and RHAMM monoclonal antibody (mAb). The table shows calculated association rates ($K_{ON}$), dissociation rates ($K_{OFF}$) and binding constants ($K_D$). Errors are standard deviation of the mean $K_D$.

FIG. 5 B is a graph which shows competitive displacement of dye-labelled HA by six selected non-labelled RHAMM-binding peptides (SEQ ID NOs: 1, 3, 9, 11, 12 and 14) of the present invention by HA to immobilized RHAMM-CT. Data shows mean of three measurements in two independent experiments.

FIG. 5 C is a graph which shows ELISA binding assay of six fluorescein-conjugated RHAMM-binding peptides SEQ ID NOs: 1, 3, 9, 11, 12 and 14 (corresponding to SEQ ID NOs: 25, 27, 29, 31, 33 and 35 respectively) of the present invention and purified CD44 or RHAMM-CT. Data shows mean of three measurements in two independent experiments.

FIG. 6 B is a graph which illustrates quantification of uptake of fluorescein-conjugated SEQ ID NOs: 1, 9 and 14 (SEQ ID NOs: 25, 29, 35) in breast tumour cells (MDA-MB-231). Each bar represents the mean of 1048 measurements from each of the three experiments. All treatment groups were significantly higher (p<0.001) compared to groups which received anti-RHAMM treatment. Data were analyzed using ANOVA and errors are standard deviation of the mean

FIG. 8 A is an amino acid sequence of HA-binding domain (aa 718-750; SEQ ID NO: 19) of RHAMM Basic amino acid residues required for HA binding are underlined.

FIG. 8 B is an amino acid sequence alignment of four RHAMM-binding peptides (SEQ ID NOs: 1, 3, 9 and 11). Identical sequences are highlighted in grey while semi-conserved residues are boxed in white. Acidic amino acid residues which may interact with the basic amino acid residues on RHAMM via ionic bonding are underlined.

FIG. 10 B illustrates the competitive displacement of twelve alanine-substituted fluorescein-conjugated peptides of SEQ ID NO: 1 (SEQ ID NO: 25) by HA to immobilized RHAMM (SEQ ID NOs: 1 and 36-47, respectively, from left to right). Negative control (no immobilized RHAMM was subtracted from each measurement and all data shows mean of three measurements in two independent experiments.)

FIG. 14 B shows quantification of SEQ ID NO: 9 of the present invention by PC3mLN4 human prostate cancer cells. Data shows no statistical difference in cells which receive no antibody treatment (a) and cells blocked with anti-CD44 (b). Uptake of the probe drastically decreased in cells treated with anti-RHAMM antibody (c).

FIG. 15 B is a RP-HPLC chromatogram of purified Ga-DOTA-conjugated SEQ ID NO: 1 peptide at 9.73 minutes.

FIG. 15 C is an ESI mass spectrum of purified Ga-DOTA-conjugated SEQ ID NO: 1 peptide.

FIG. 16 B is a RP-HPLC chromatogram of purified $Re(CO)_3^+$-coordinated SEQ ID NO: 1 peptide at 11.06 minutes.

FIG. 16 C is an ESI mass spectrum of purified $Re(CO)_3^+$-coordinated SEQ ID NO: 1 peptide.

FIG. 17 B illustrates the competitive displacement of eleven alanine-substituted fluorescein-conjugated peptides of SEQ ID NO: 14 (SEQ ID NO: 35) by HA to immobilized RHAMM (SEQ ID NOs: 48-55, 14 and 56-58, respectively, from left to right). Negative control (no immobilized RHAMM was subtracted from each measurement and all data shows mean of three measurements in two independent experiments.)

DETAILED DESCRIPTION OF THE INVENTION

Definitions

Figure 1:
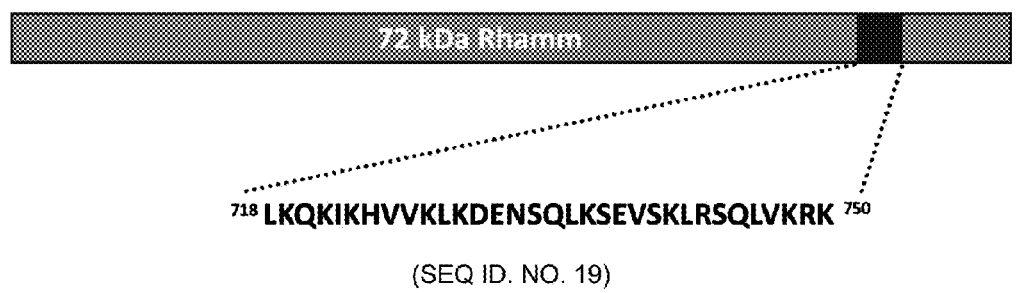
FIG. 1 A illustrates a diagram of 72 kDa RHAMM protein containing the HA-binding domain (amino acid residues 718-750, SEQ ID NO: 19) necessary for RHAMM/hyaluronan (HA) interaction.
Figure 1:
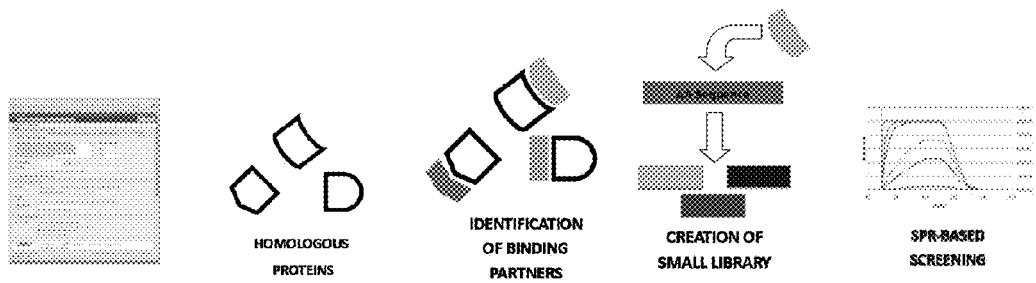

The following standard one letter and three letter abbreviations for the amino acid residues may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenyalanine; P, Pro—Proline; S, Ser—Serine; T, Thr—Threonine; W, Trp—Tryptophan; Y, Tyr—Tyrosine; and V, Val—Valine.

"Analog" includes any peptide having an amino acid residue sequence substantially identical to the sequence of the RHAMM-binding peptides of the present invention in which one or more residues have been conservatively substituted with a functionally similar residue and which displays the ability to mimic a HA binding peptide.

"Derivative" refers to a peptide having one or more residues chemically derivatized by reaction of a functional side group. Such derivatized molecules may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "fragment" refers to any subject peptide having an amino acid residue sequence shorter than that of a peptide whose amino acid residue sequence is shown herein.

The term "isolated peptide" or "isolated DNA" may be defined as a peptide or DNA molecule, as the case may be, which is substantially separated from other cellular components which may naturally accompany the peptide and DNA molecules. The term includes, without limitation, recombinant or cloned DNA isolates and chemically synthesized analogs or analogs biologically synthesized by heterologous systems.

The term "peptide" as used herein is defined as a chain of amino acid residues, usually having a defined sequence. As used herein the term "peptide" is mutually inclusive of the terms "peptides" and "proteins".

In this document "RHAMM" refers to a Receptor for Hyaluronic Acid Mediated Motility, also known as CD 168. RHAMM is a non-integral cell surface (CD 168) and intracellular hyaluronan binding protein that promotes cell motility in vitro and whose expression is strongly upregulated in aggressive tumors [WO 2008/140587].

The term "RHAMM-binding peptide(s)" as used herein means peptides which are capable of binding RHAMM.

"Subject" or "patient" refers to an animal, including humans, in need of treatment for a condition, disorder or disease.

Overview

The present invention relates to peptides and nucleic acid sequences coding for said peptides, which may be capable of binding RHAMM. The present invention further relates to methods of using said RHAMM-binding peptides and nucleic acid sequences coding for said RHAMM-binding peptides in the treatment of diseases, conditions or disorders that may be associated with RHAMM expression in cells. The RHAMM-binding peptides of the present invention may be used in probes which may be capable of identifying cells expressing RHAMM. The present invention further relates to methods of using the RHAMM-binding peptides for the identification of samples which may include cells expressing RHAMM.

Advantages of the present invention include: (a) Novel small peptides have been discovered that bind RHAMM with specificity; (b) To the inventors' knowledge tumor progenitor cells have not been directly imaged. The novel peptides may be used as molecular imaging probes to image progenitor cell status non-invasively; (c) The capacity of the novel peptides to specifically bind RHAMM may be exploited to selectively targeting progenitor cells with a therapeutic drug agent, either directly through the ligand-receptor interaction, or indirectly by delivering a therapeutic payload to the targeted cells; (d) Binding of the peptides of the present invention to RHAMM increased epitope exposure and anti-RHAMM Mab binding, which may allow for imaging enhancement as well as to therapeutically target RHAMM positive cells.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

RHAMM-Biding Peptides

The present inventors have isolated, sequenced and characterized novel peptides of about 6 to 14 amino acid residues. As such, in one embodiment, the present invention provides for an isolated DNA coding for a peptide, said peptide having the amino acid sequence selected from the group consisting of SEQ ID NO: 1 to 17. In another embodiment, the present invention provides for an isolated peptide comprising an amino acid sequence selected from the group consisting of SEQ ID NO: 1 to SEQ ID NO: 17.

The novel peptides of the present invention may be capable of binding RHAMM. In aspects of the invention the novel RHAMM-binding peptides of the present invention may be capable of specifically binding RHAMM. In aspects of the invention the novel RHAMM-binding peptides of the present invention may be capable of binding RHAMM with substantially high affinity. In aspects of the invention the novel RHAMM-binding peptides of the present invention may be capable of specifically binding RHAMM with substantially high affinity.

In one embodiment, the novel RHAMM-binding peptides of the present invention may comprise a sequence of the formula (1):

EEXEEZ(SEQ ID NO: 18)            (1)

wherein X is selected from A or G, and Z is selected from Y or E.

In another embodiment, the novel RHAMM-binding peptides of the present invention may comprise a sequence selected from SEQ ID NO: 1 to SEQ ID NO: 17.

In another embodiment, the present invention provides for a RHAMM-binding peptide, wherein said peptide is selected from the group consisting of SEQ ID NOs: 1, 3, 9, 10, 11, 12 and 14.

In another embodiment, the present invention provides for a RHAMM-binding peptide, wherein said peptide is selected from the group consisting of SEQ ID NOs: 1, 9 and 14.

In one embodiment, the peptides of the present invention may be derived from the carboxy terminal tails (CTT) region of tubulin. In another embodiment RHAMM-binding peptides may be derived from for sequences directly adjacent to the tubulin's CTT region. Surprisingly, the inventors discovered that RHAMM shares structural and functional similarities with proteins which may be essential to the maintenance of mitotic spindles. Furthermore, the inventors discovered that RHAMM's HA binding domain may show sequence homology to the tubulin binding domain of many kinesins and microtubule associated proteins (MAPs). The CTT region of tubulin has been shown to interact with conventional kinesins and MAPs.

Figure 6A:
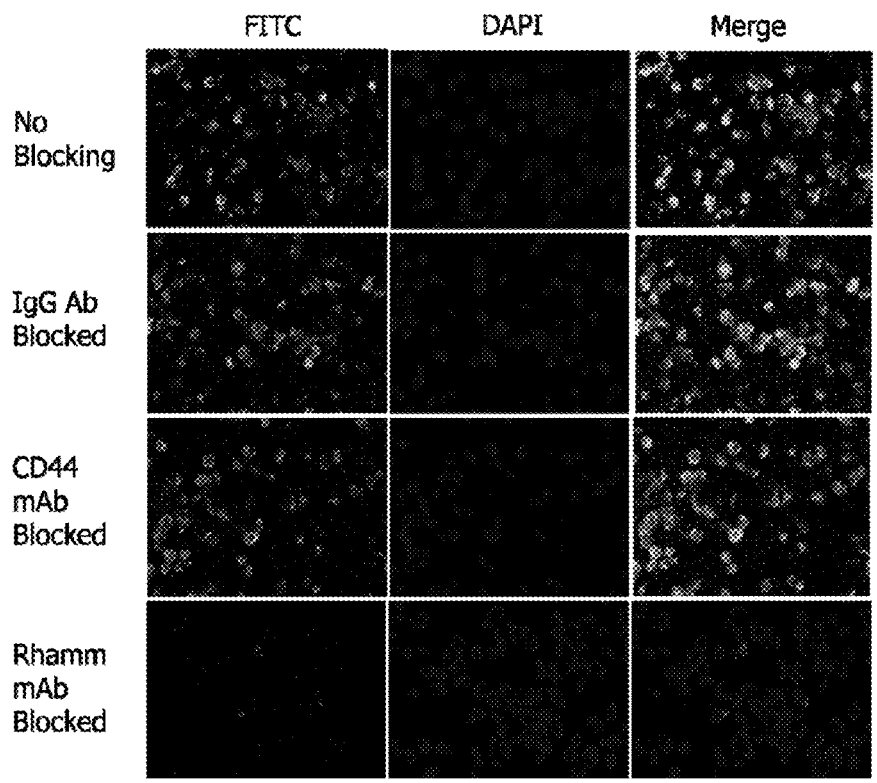
FIG. 6 A is a microphotograph which illustrates visualization of uptake of fluorescein-conjugated SEQ ID NO: 14 (SEQ ID NO: 35) in breast tumour cells (MDA-MB-231) using fluorescence imaging. DAPI channel denotes nucleus while FITC channel illustrates localization of the fluorescein-labelled peptide.
Figure 6B:
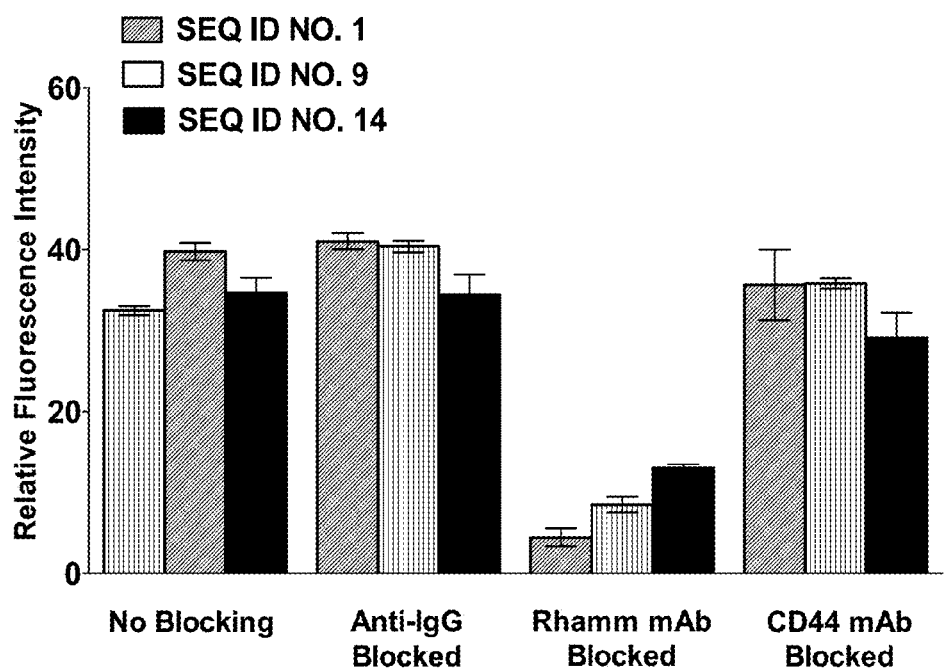
Figure 7:
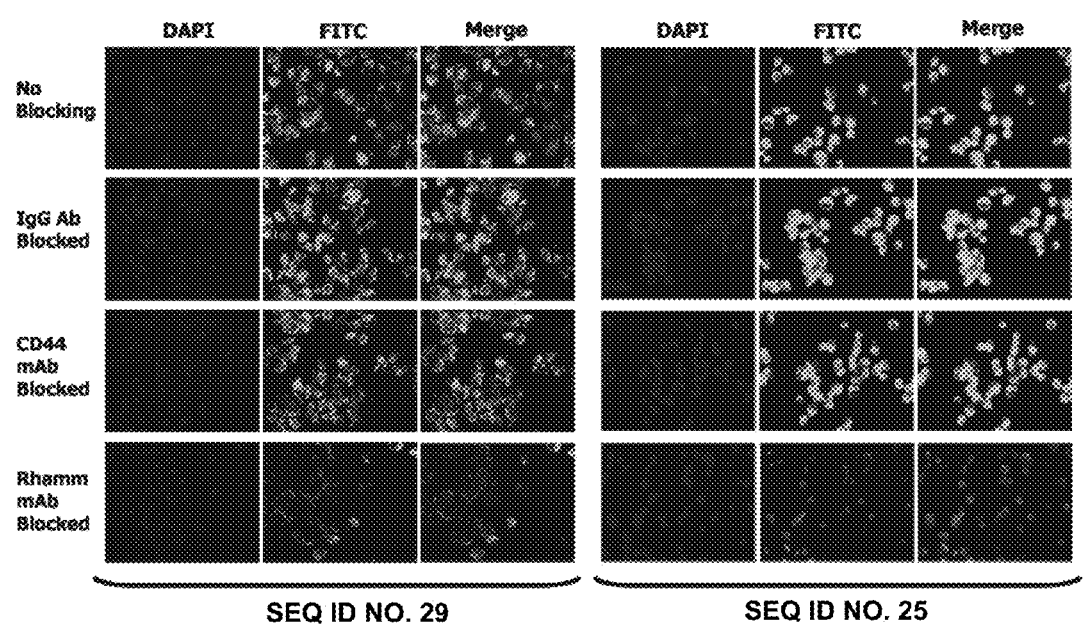
FIG. 7 is a microphotograph which illustrates visualization of uptake of FITC-conjugated SEQ ID NO: 1 and SEQ ID NO: 9 (SEQ ID NOs.: 25 and 29) in breast tumour cells (MDA-MB-231) using fluorescence imaging. DAPI channel denotes nucleus while FITC channel illustrates localization of the fluorescein-labelled peptide.
Figure 13:
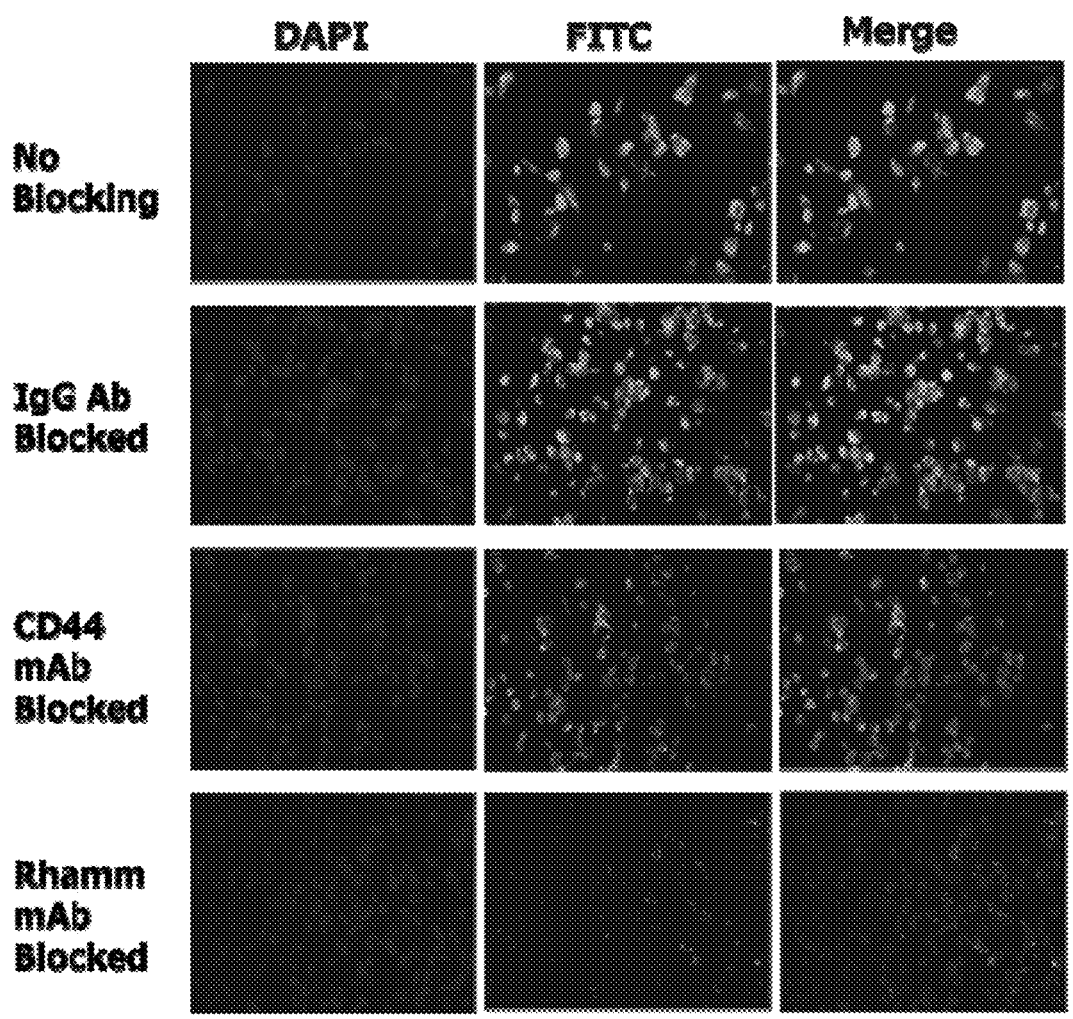
FIG. 13 is a photomicrograph illustrating uptake fluorescein-conjugated peptide SEQ ID NO: 1 (SEQ ID NO: 25) in ovarian tumor cells using fluorescence microscopy. DAPI channel denotes nucleus while FITC channel illustrates localization of the fluorescein-labelled peptide.
Figure 14A:
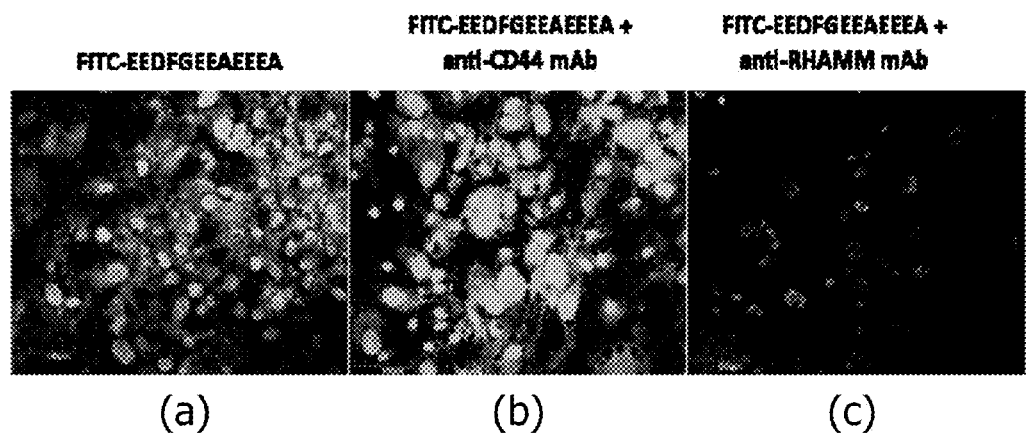
FIG. 14 A shows (a) uptake of the fluorescein-conjugated SEQ ID NO: 9 (SEQ ID NO: 29) of the present invention by PC3mLN4 human prostate cancer cells using fluorescence microscopy, (b) uptake of fluorescein-SEQ ID NO: 9 is not blocked by a specific anti-CD44 mAb, however, (c) uptake of fluorescein-conjugated SEQ ID NO: 9 is blocked by a specific anti-RHAMM mAb.
Figure 14B:
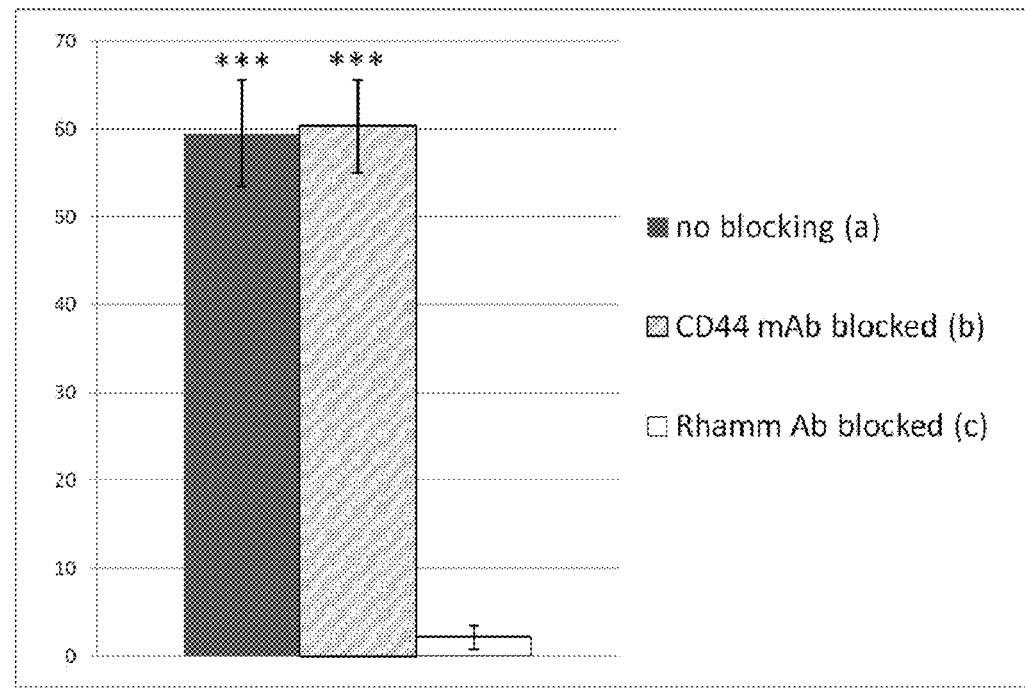
Figure 15A:
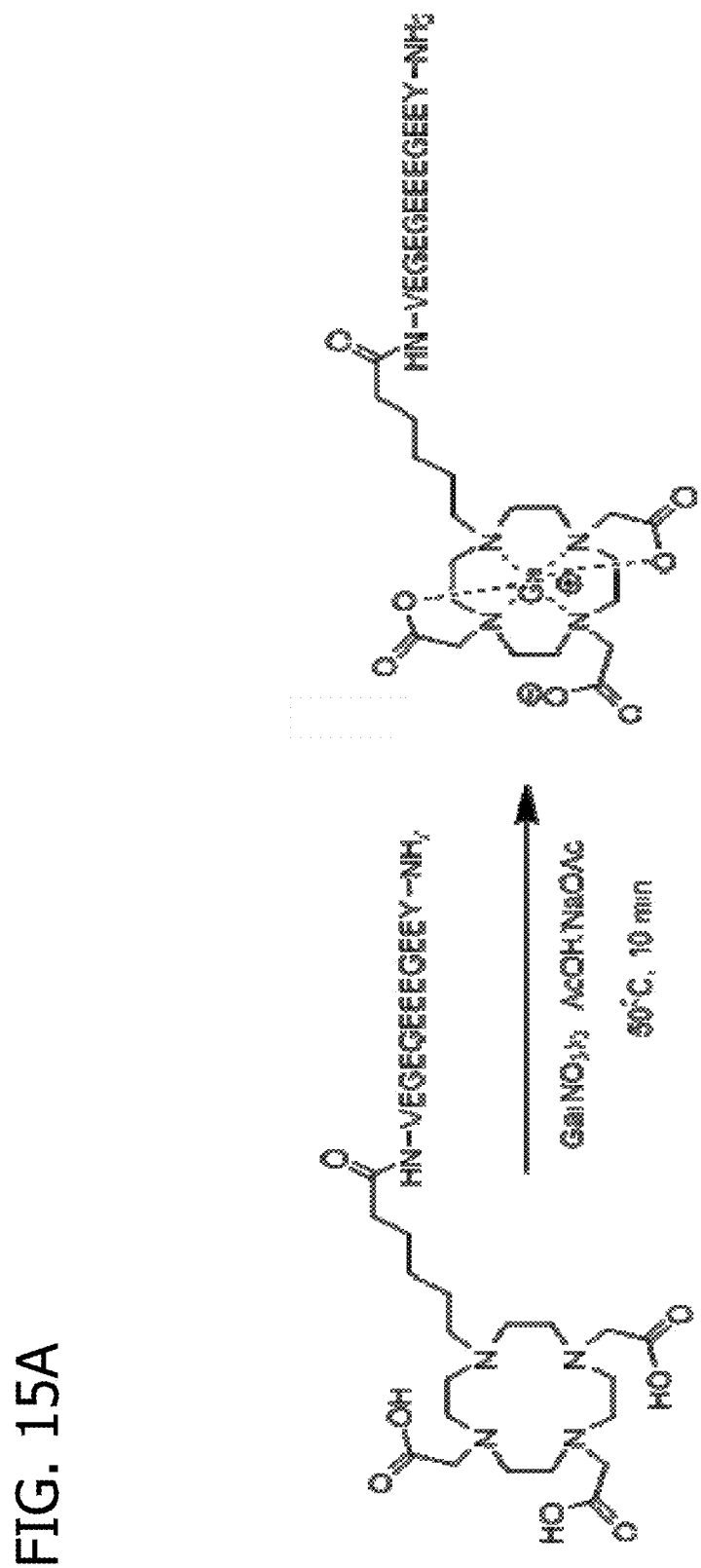
FIG. 15 A illustrates the synthesis of Ga-DOTA-conjugated SEQ ID NO: 1 peptide.
Figure 15B:
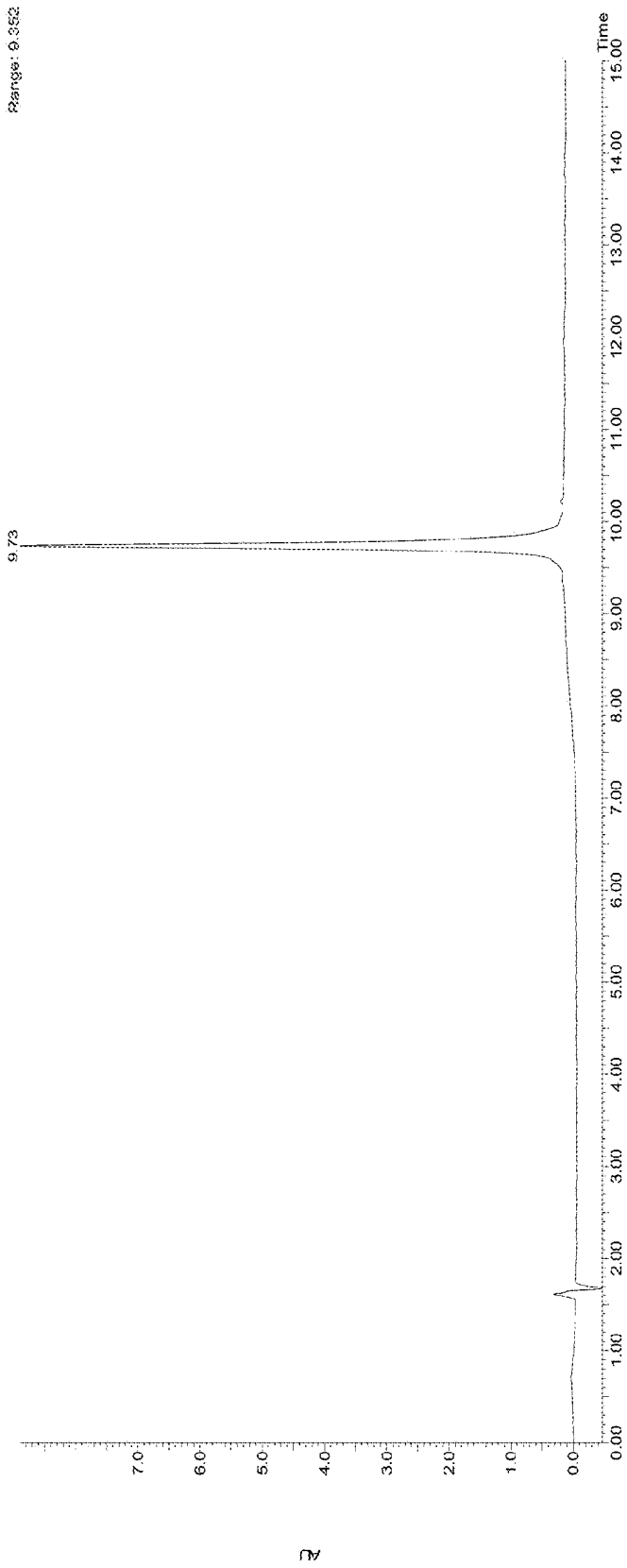
Figure 15C:
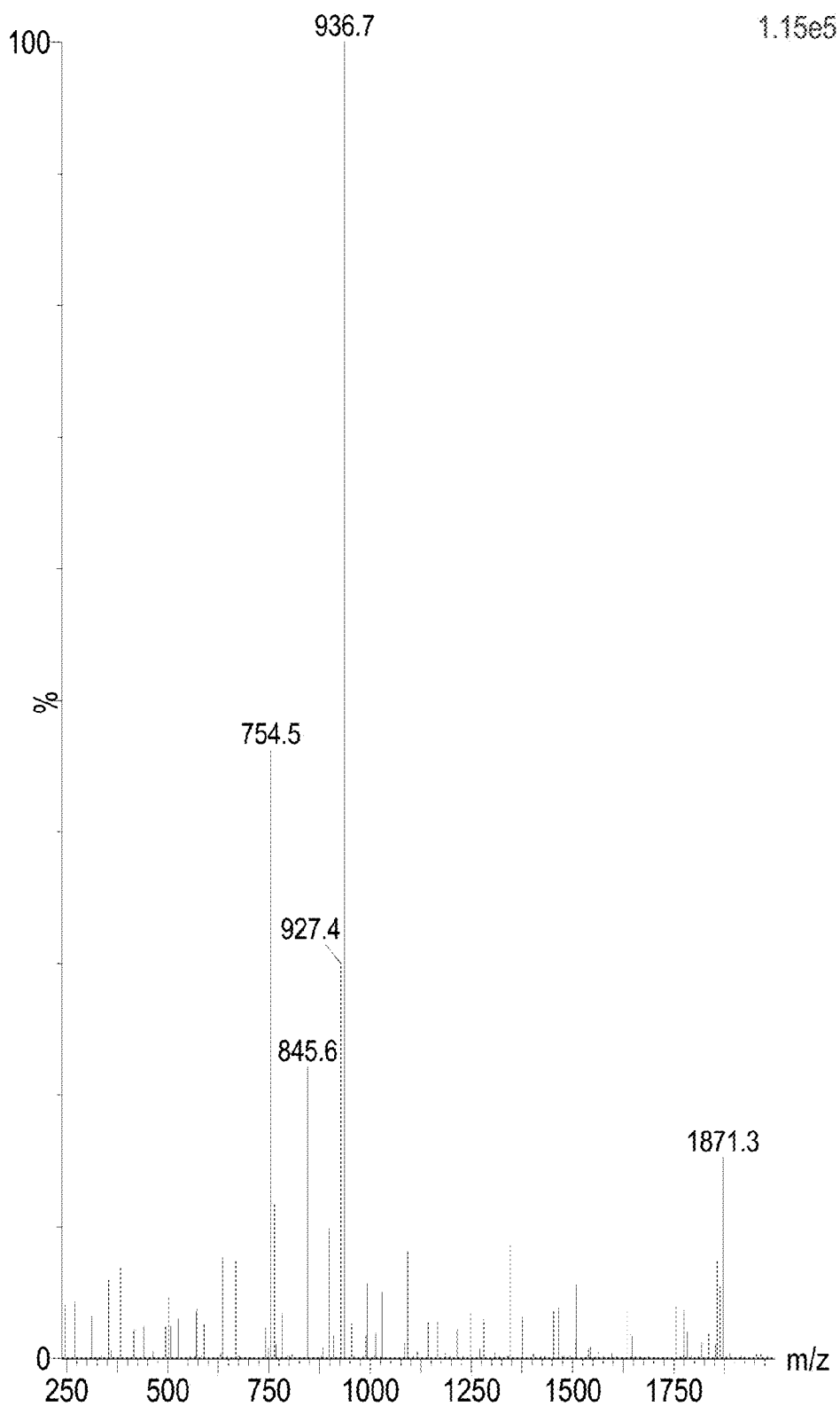

By way of example, human breast cancer cell line MDA-MB-231, which is known to express RHAMM, showed intra-cellular fluorescence when incubated with dye-conjugated peptides of the present invention, as illustrated in FIG. 6A and FIG. 7. Cells blocked with anti-RHAMM showed about 65% to about 85% reduction in intra-cellular fluorescence as illustrated in FIG. 6 B. Other RHAMM expressing cancer cells such as PC3mLN4 and patient derived ovarian tumor cells also show intra-cellular fluorescence when incubated with RHAMM peptides of the present invention, as illustrated in FIG. 13 and FIGS. 14A and 14B.

The inventors further discovered that the binding of the RHAMM-binding peptides of the present invention to RHAMM may increase epitope exposure and anti-RHAMM monoclonal antibody (mAb) binding. This capacity of the RHAMM-binding peptides of the present invention to increase epitope exposure to anti-RHAMM mabs may be used therapeutically as well as for image enhancement. As such, the peptides of the present invention may be used, for example, to "activate" available RHAMM, for example in tumors (but not limited to this disease). Then, a therapeutic or imaging (Fab fragment for example) anti-RHAMM mAb may be administered and may be more effective in targeting the (tumor) cell expressing RHAMM.

Taken together, the present invention demonstrates a set of RHAMM-binding peptides which in aspects may be derived from the CTT of tubulin sequences and in other aspects may be based on artificial peptide sequences.

The peptides of the present invention may be modified by the addition cysteine residues to one or both ends of the peptides to cyclize the peptides by the formation of disulfide bond formation. The peptides of the present invention may be modified by the addition of phosphorus and acetyl groups. Phosphorylation is one of the most common protein modifications that occur in animal cells [4]. It occurs most commonly on threonine, serine and tyrosine residues and plays critical roles in the regulation of many cellular processes including: cell cycle, growth, apoptosis and differentiation [4]. This procedure is possible because some of the peptides of the present invention contain tyrosine and because an acyl group may be added to N-terminal amino acid [5]. The aromatic amino acids phenylalanine, tryptophan and tyrosine in the peptides of the invention may be substituted with other aromatic amino acids to evaluate their effects on peptide activities. Similarly, aliphatic amino acids such as glycine, alanine, valine, isoleucine and leucine in the peptides of the invention may be substituted with other aliphatic amino acids to evaluate their effects on peptide activities.

The peptides of the invention may be of about 6 to about 14 amino acids in length and may include any ranges of length therein (i.e 6-13, 6-12, 6-11, 6-10, 6-9, 6-8, 6-7, 7-13, 7-12, 7-11, 7-10, 7-9, 7-8, 8-13, 8-12, 8-11, 8-10, 8-9, 9-14, 9-13, 9-12, 9-11, 9-10, 10-11, 10-12, 10-13 and 10-14) as is understood by one of skill in the art. Peptides of over about 14 amino acids in length may also be encompassed by the present invention. The length of peptide being only restricted by its ability to bind RHAMM. The peptides of the invention may also include dimers and trimers of the peptides as well as additional stabilizing flanking sequences as is understood by those of skill in the art and described for example in U.S. Pat. No. 5,824,315 and U.S. Pat. No. 6,184,204 (the disclosures of which are incorporated herein by reference in their entirety). A multimer according to the invention can either be a homomer, consisting of a multitude of the same peptide, or a heteromer consisting of different peptides. As stated, the amino acid sequences of the peptides according to the invention may be flanked by random amino acid sequences. Preferred may be flanking sequences which have a stabilizing effect on the peptides, thus increasing their biological availability. In addition, other peptidomimetics may also be useful in the peptides of the present invention. The peptides of the invention may also encompass peptides which may have been modified by, for example, phosphorylation, glycosylation, pegylation or lipidation. Furthermore, the peptides of the present invention may also encompass functionally equivalent variants or analogues of the peptides of the present invention. As such, this may include but not be limited to peptides with partial sequence homology, peptides having one or more specific conservative and/or non-conservative amino acid changes and peptide conjugates which do not alter the biological or structural properties of the peptide (i.e. the ability to bind to RHAMM).

In terms of functional analogues, it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity, which, in this case, would include the ability to bind to RHAMM. A plurality of distinct peptides/proteins with different substitutions may easily be made and used in accordance with the invention. It is also understood that certain residues may be particularly important to the biological or structural properties of a protein or peptide such as residues in the receptor recognition region, such residues of which may not generally be exchanged.

Functional analogues may be generated by conservative or non-conservative amino acid substitutions. Amino acid substitutions may be generally based on the relative similarity of the amino acid side-chain substituents, for example, their hydrophobicity, hydrophilicity, charge, size and the like. Thus, within the scope of the invention, conservative amino acid changes means an amino acid change at a particular position which may be of the same type as originally present; i.e. a hydrophobic amino acid exchanged for a hydrophobic amino acid, a basic amino acid for a basic amino acid, etc. Examples of conservative substitutions may include, without limitation, the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes may result in functional analogues in that they may not significantly alter the overall charge and/or configuration of the peptide. Examples of such conservative changes are well-known to the skilled artisan and are within the scope of the present invention. Conservative substitution may also include the use of a chemically derivatized residue in place of a non-derivatized residue provided that the resulting peptide is a biologically functional equivalent to the peptides of the invention. Therefore, the peptides of the present invention may encompass a peptide having an amino acid sequence that differs from SEQ ID NOs: 1-17. The peptides of the invention may also encompass a peptide having an amino acid sequence that may differ from SEQ ID NOs: 1-17 by a single mutation, where the single mutation represents a single amino acid deletion, insertion or substitution.

Figure 10A:
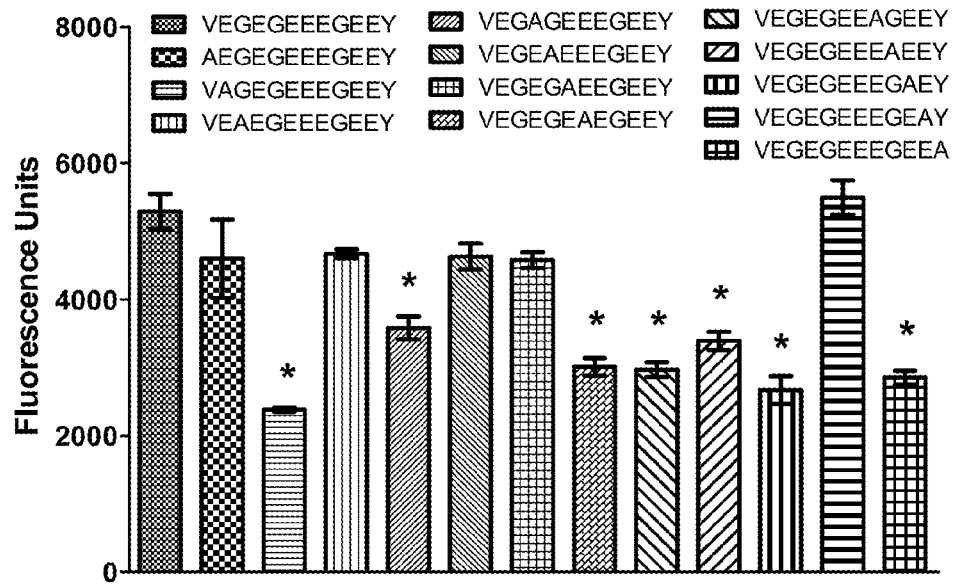
FIG. 10 A is a graph which illustrates the affinity of alanine-substituted fluorescein-conjugated peptides of SEQ ID NO: 1 (SEQ ID NO: 25) to RHAMM (SEQ ID NOs: 1 and 36-47, respectively, in columns from left to right). Asterisks show significant decrease (p<0.01) in observed fluorescence due to alanine substitutions of residues important for RHAMM binding (no immobilized RHAMM was subtracted from each measurement and all data shows mean of three measurements in two independent experiments).
Figure 10B:
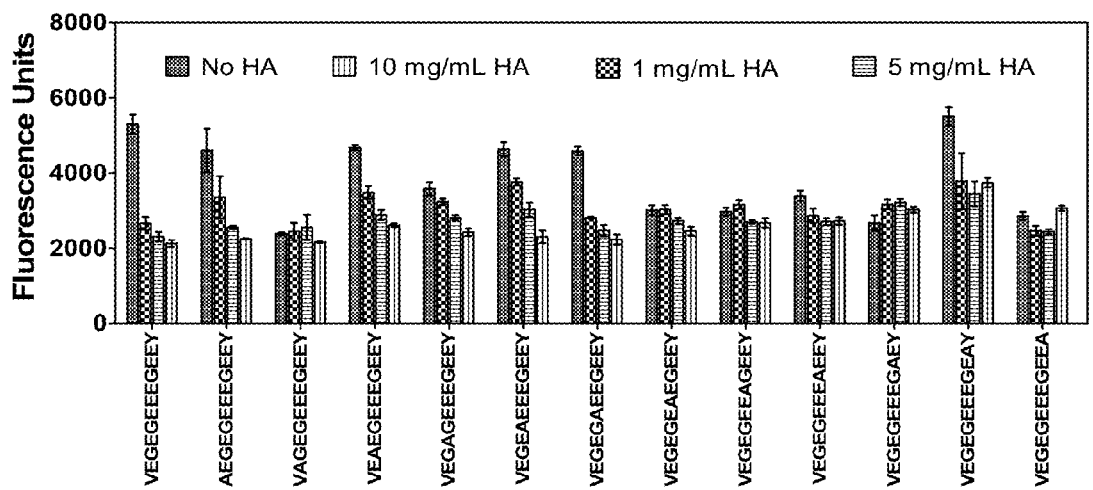

FIG. 10 A and FIG. 10 B, for example, illustrate that in the case of RHAMM-binding peptide SEQ ID NO: 1, alanine substitution at positions 1, 3, 5, 6 and 11 do not appear to affect proper binding of the substituted RHAMM-binding peptide to RHAMM.

Figure 17A:
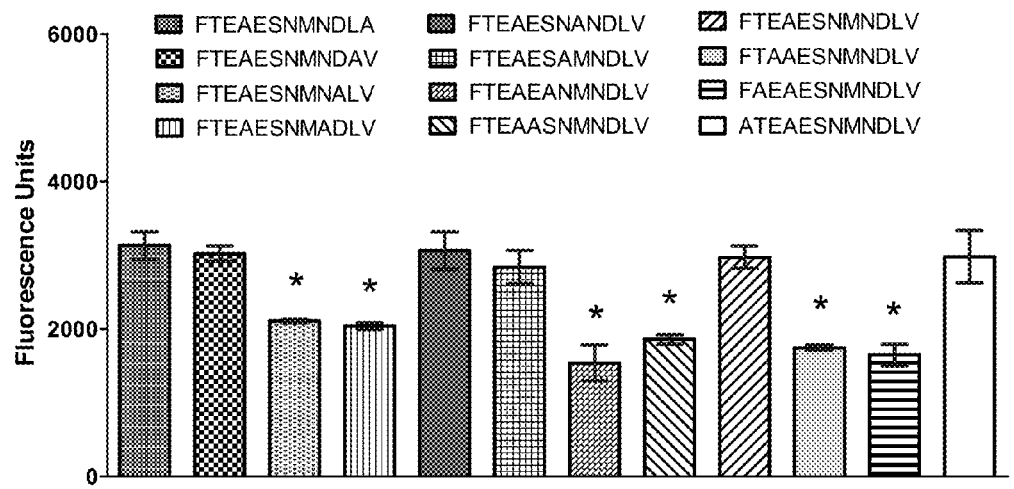
FIG. 17 A illustrates the affinity of alanine-substituted fluorescein-conjugated peptides of SEQ ID NO: 14 (SEQ ID NO: 35) to RHAMM (SEQ ID NOs: 48-55, 14 and 56-58, respectively, in columns from left to right). Asterisks show significant decrease (p<0.01) in observed fluorescence due to alanine substitutions of residues important for RHAMM binding (no immobilized RHAMM was subtracted from each measurement and all data shows mean of three measurements in two independent experiments.)
Figure 17B:
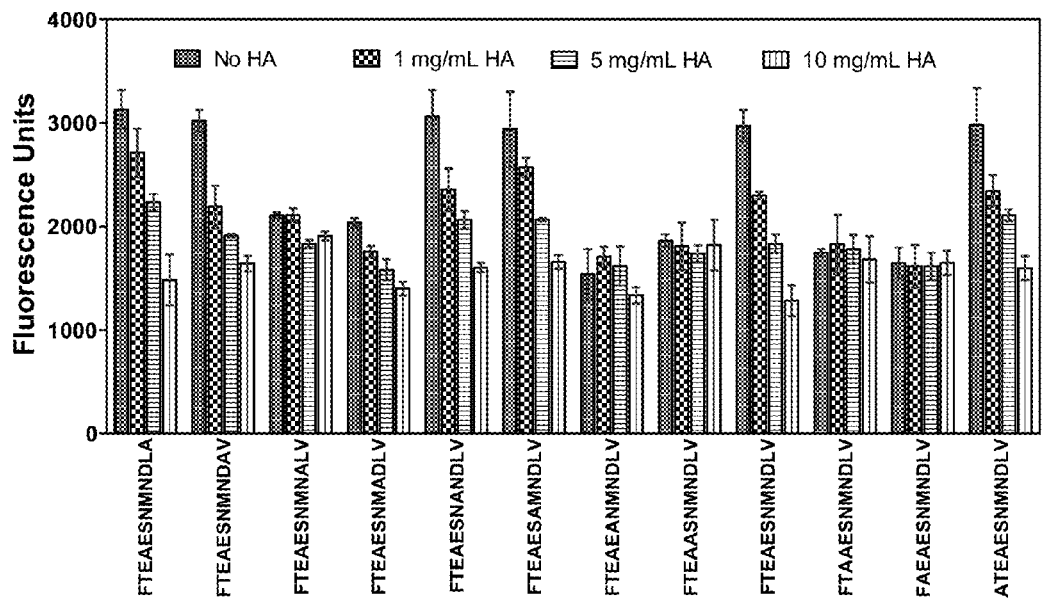

FIG. 17 A and FIG. 17 B, for example, illustrate that in the case of RHAMM-binding peptide SEQ ID NO: 14, alanine substitution at positions 1, 4, 7, 8, 11 and 12 do not appear to affect proper binding of the substituted RHAMM-binding peptide to RHAMM.

Preparation of the RHAMM-Binding Peptides

The peptides of the present invention may be made by methods known to those of skill in the art most notably and preferably by chemical synthesis using techniques well known in the chemistry of proteins such as solid phase synthesis [6, 7, 8, which are hereby incorporated by reference] or synthesis in homogenous solution[9, which is hereby incorporated by reference] to generate synthetic peptides.

Alternatively, the peptides of the invention may be made by the use of recombinant DNA techniques known to one skilled in the art.

It is further contemplated that the invention encompasses vectors which may include nucleic acids coding for at least one of the peptides of the present invention.

Isolation of the RHAMM-Binding Peptides

RHAMM-binding peptides may be isolated by assaying a sample for peptides that bind to RHAMM. Any assay system or testing method that detects protein-protein interactions may be used including, without limitation, co-immunoprecipitation, crosslinking and co-purification through gradients or chromatographic columns. Biological samples and commercially available libraries may be tested for RHAMM-binding peptides. For example, labelled RHAMM may be used to probe phage display libraries as is described in greater detail in Example 1. In addition, antibodies prepared to the peptides of the invention may be used to isolate other peptides with RHAMM binding affinity. For example, labelled antibodies may be used to probe phage display libraries or biological samples.

Additionally, a DNA sequence encoding a RHAMM protein may be used to probe biological samples or libraries for nucleic acids that encode HA-binding proteins.

Compositions

In one embodiment, the present invention provides for compositions which may comprise one or more RHAMM-binding peptides of this invention for administration to subjects in a biologically compatible form suitable for administration in vivo. In another embodiment, the present invention provides for compositions which may comprise one or more RHAMM-binding peptides for use to study samples in vitro. Samples which may be used include, without limitation, cells, tissues and organs.

By "biologically compatible form suitable for administration in vivo" is meant a form of the substance to be administered in which any toxic effects are outweighed by the therapeutic effects. The substances may be administered to any animal, preferably, humans. Administration of a therapeutically active amount of the pharmaceutical compositions of the present invention, or an "effective amount", may be defined as an amount effective at dosages and for periods of time, necessary to achieve the desired result of eliciting an immune response in a human. Suitable administration routes may be intramuscular injections, subcutaneous injections, intravenous injections or intraperitoneal injections, oral and intranasal administration.

Acceptable carriers are well known to those skilled in the art and include, for example, sterile saline, lactose, sucrose, calcium phosphate, gelatin, dextrin, agar, pectin, peanut oil, olive oil, sesame oil and deionised water.

Furthermore the composition according to the invention may comprise one or more stabilizers such as, for example, carbohydrates including sorbitol, mannitol, starch, sucrose, dextrin and glucose, proteins such as albumin or casein, and buffers like alkaline phosphates. Furthermore, the composition of the present invention may comprise one or more adjuvants which may enhance the anti cell proliferative properties of the peptides of the invention.

Compositions for injection may include, albeit not exclusively, the peptides or nucleic acids of the present invention in association with one or more pharmaceutically acceptable vehicles or diluents, and contained in buffered solutions with a suitable pH and iso-osmotic with the physiological fluids. Any pharmaceutically suitable diluent may be used in the composition for injections: distilled water, physiological or a salt solution, and/or a buffer solution. The composition for injections may be prepared by conventional volume-weight procedures. A certain amount of the peptide may be diluted to the necessary volume with a diluent or solvent. The solution may then filtered through sterilized filters, bottled or ampouled. The resultant solution may be a stable transparent liquid, and may not contain any chemical or other impurities.

Detection Probes

Detection of RHAMM expression in samples, including, without limitation, cells, tissues or organs, may be carried out by a suitable probe. The probe may include at least a RHAMM-binding peptide of the present invention and a detectable label. The detectable label may be capable of being detected by a detection means. The detection means may be any detection technique which may be capable of providing a measurable response to the detectable label. In aspects of the invention, the measurable response may be provided in the form of an image. The detectable label may allow detection of the location of the RHAMM positive cells with a suitable detection means. The probe of the present invention may allow following movement and development of RHAMM positive cells. As such, in one embodiment, the probes of the present invention may be used, without limitation, to study RHAMM positive cells, in diagnosis and prognosis methods.

Methods of preparing probes are well known to those of skill in the art [10, 11, which are hereby incorporated by reference].

Methods of labelling are well known to those of skill in the art. Preferred labels may be those which are suitable for use in in vivo imaging. The anti-RHAMM probes may be detectably labelled prior to detection. Alternatively, a detectable label which may bind to the hybridization product may be used. Such detectable labels may include, without limitation, any material having a detectable physical or chemical property and have been well-developed in the field of immunoassays. A label for use in the present invention may be any composition detectable by detection means such as, without limitation, spectroscopic, photochemical, biochemical, immunochemical, or chemical means.

Labels which may be used in the present invention include biotin-based label, magnetic label (e.g. DYNABEADS™), radioactive label (e.g. $^3$H, $^{35}$S, $^{32}$P, $^{51}$Cr, or $^{125}$I), fluorescent label (e.g. fluoroscein, rhodamine, Texas Red, etc.), electron-dense reagents (e.g. gold), enzymes (e.g. alkaline phosphatase, horseradish peroxidase, or others commonly used in an ELISA), digoxigenin, or haptens and proteins for which antisera or monoclonal antibodies may be available (for example the peptides of the present invention may be made detectable by, for example, incorporating a radiolabel into the peptide, and used to detect antibodies specifically reactive with the peptide). The RHAMM-binding peptides of the invention may be provided with a carrier such as for example coupled to bovine serum albumin (BSA) or keyhole limpet haemocyanin.

The RHAMM-binding peptides may be covalently or non-covalently coupled to a solid carrier such as a microsphere of gold or polystyrene, a slide, chip or to a wall of a microtitre plate. The RHAMM-binding peptides may be labelled directly or indirectly with a label selected from but not limited to biotin, fluorescein and an enzyme such as horseradish peroxidase.

The particular label used may not be critical to the present invention, so long as it does not interfere with the formation of RHAMM/RHAMM-binding peptide complexes. However, in one embodiment, the imaging component may be a radionuclide (e.g. $^{18}$F, $^{11}$C, $^{13}$N, $^{64}$Cu, $^{68}$Ga, $^{123}$I, $^{111}$In, $^{99m}$Tc, etc.) due to the ease of using such techniques as SPECT, CT and PET imaging for in vivo detection of RHAMM/RHAMM-binding peptide complexes and tumor progenitor cells. Decision as to appropriate imaging component for agents used in SPECT or PET imaging may also be determined by whether the radionuclide is generated by generator or cyclotron or is an chelator or organic/halide. FIGS. 15A-15C and 16A-16C illustrate the synthesis and mass spectrometry characterization of Ga-DOTA-conjugated peptide SEQ ID NO: 1, and of Re(CO)$_3^+$-coordinated peptide SEQ ID NO: 1.

A direct labelled probe, as used herein, may be a probe to which a detectable label is attached. Because the direct label is already attached to the probe, no subsequent steps may be required to associate the probe with the detectable label. In contrast, an indirect labeled probe may be one which bears a moiety to which a detectable label is subsequently bound, typically after the RHAMM-binding peptide is hybridized with the target RHAMM.

In another embodiment, monoclonal antibodies (mAb) which may recognize any of the RHAMM-binding peptides of the invention may also be made and used to detect the presence of the RHAMM-binding peptides in a sample. Mab may provide a rapid and simple method of testing the compositions of the invention for their quality. In general, methods for the preparation of antibodies are well known. For example, methods to produce mAb which specifically recognize the RHAMM-binding peptides of the invention are well known to those of skill in the art. In general, peptides are injected in Freund's adjuvant into mice. After being injected 9 times over a three week period, the mice spleens are removed and re-suspended in phosphate buffered saline (PBS). The spleen cells may serve as a source of lymphocytes, some of which may be producing antibody of the appropriate specificity. These may then fused with a permanently growing myeloma partner cell, and the products of the fusion may be plated into a number of tissue culture wells in the presence of a selective agent such as HAT. The wells may then be screened to identify those containing cells making useful antibody by ELISA. These may then be freshly plated. After a period of growth, these wells may again be screened to identify antibody-producing cells. Several cloning procedures may be carried out until over 90% of the wells contain single clones which are positive for antibody production. From this procedure a stable lines of clones may be established which produce the mAb. The mAb may then be purified by affinity chromatography using Protein A or Protein G Sepharose (see also, U.S. Pat. Nos. 4,609,893; 4,713,325; 4,714,681; 4,716,111; 4,716,117; and 4,720,459).

Applications of the RHAMM-Binding Peptides

The present invention may encompass detection, imaging, diagnostic and therapeutic strategies which may involve, without limitation, targeting RHAMM with the RHAMM-binding peptides of the present invention, which may disrupt the formation of RHAMM/ligand complexes which may play a role in stimulating the ligand-RHAMM mediated cell motility response. These methods may be used in combination with other known therapies for treating conditions related to a pathogenic condition, inflammation and pathogenic infections.

1. Detection of RHAMM Positive Cells

Figure 9:
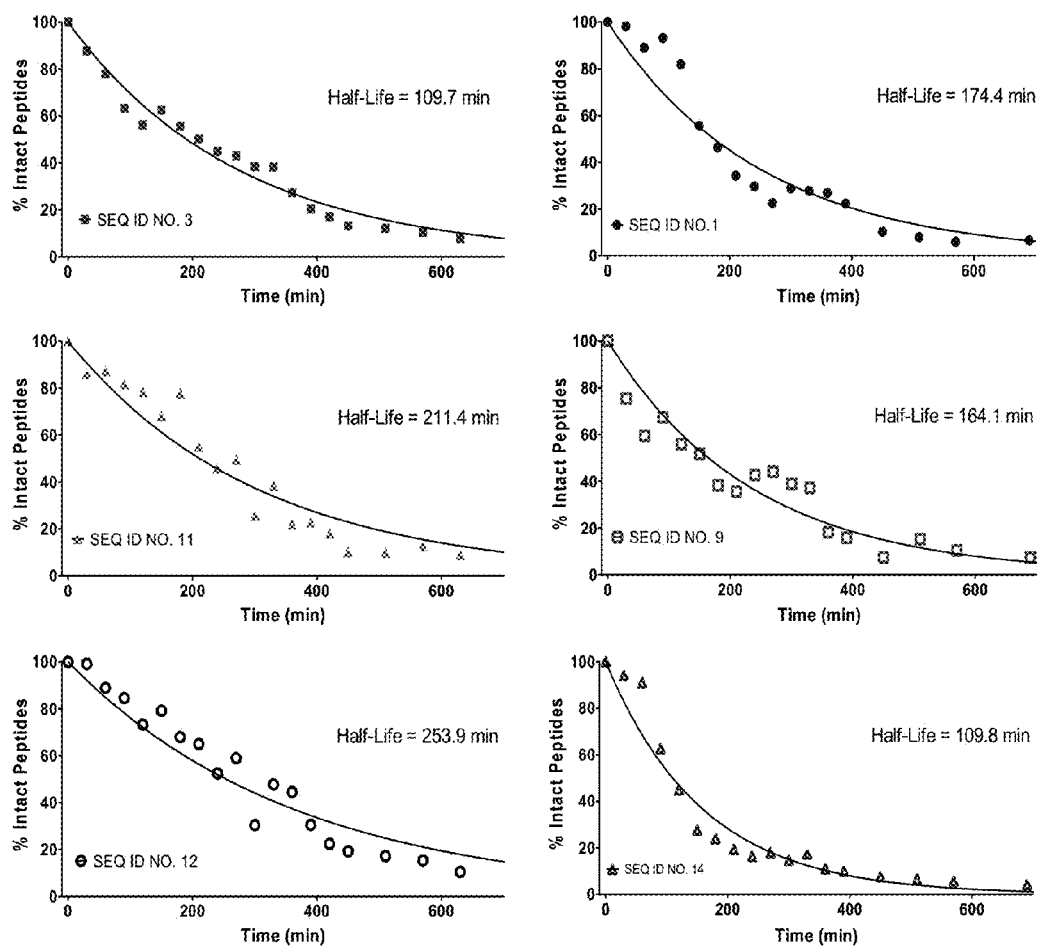
FIG. 9 illustrates serum stability study of SEQ ID NOs: 1, 3, 9, 10, 12 and 14. Graphs show percent intact peptides (as detected by RP-HPLC) at 30 minutes increments for 11 hours. Data were fitted to a first order decay curve.

With reference to FIG. 9, the RHAMM-binding peptides of the present invention have been shown to have moderate stability in a biological environment (about 110 to about 250 minutes half-life), which may be long enough to facilitate in vitro or in vivo imaging.

In one embodiment of the present invention the RHAMM-binding peptides may be used in methods to identify RHAMM positive cells. The method for identifying RHAMM positive cells may include contacting cells with a probe of the present invention and applying a suitable detection technique for detecting the detectable label in the cells. Identification of the RHAMM positive cells may be determined based on detection of the detectable label with the detection technique.

In another embodiment, a method of detecting RHAMM expression in tissues or organs of a subject is provided. The method may comprise: (a) administering a probe according to the present invention to the subject; (b) applying the detection technique for detecting the label in the tissues or organs of the subject.

Since tumorigenic progenitor cells may be characterized by RHAMM expression, in another embodiment, the RHAMM-binding peptides of the present invention may be used in diagnostic methods to determine whether samples such as tumor biopsies may include tumorigenic progenitor cells, which may put the cancer patient at risk for developing metastases. One such diagnostic method may comprise using one or more of RHAMM-binding peptides to detect for the presence of RHAMM in a sample. RHAMM positive samples may be indicative that the sample contains cancer progenitor cells.

A method for diagnosing a patient of cancer according to one embodiment of the present invention may comprise: (a) obtaining a tissue sample from the patient; (b) contacting said sample with a probe of the present invention; (c) applying the detection technique for detecting the probe's detectable label in the sample. Detection of RHAMM expression in the sample may be indicative of a cancer diagnosis.

A method for diagnosing a patient of cancer according to another embodiment of the present invention may comprise: (a) administering a probe according to the present invention to the subject; and (b) applying the detection technique for detecting the probe's label in the tissues or organs of the subject. Detection of RHAMM in the subject may be indicative of a cancer diagnosis.

A method for determining a prognosis for a cancer patient according to another embodiment of the present invention may comprise: (a) obtaining a tumor tissue sample from the patient; (b) contacting said sample with a probe of the present invention; (c) applying the detection technique for detecting the probe's label in the sample; and (d) determining the prognosis of the patient. The prognosis may predict a probability of aggressiveness or metastasis of the cancer in the patient. Detection of RHAMM expression in the sample may be indicative of a poor prognosis.

In another embodiment, the present invention provides for a method for determining a course of treatment for a cancer patient. The method may comprise: (a) obtaining a tumor tissue sample from the patient; (b) contacting said sample with a probe of the present invention; (c) applying the detection technique for detecting the probe's label in the sample; and (d) determining the prognosis of the patient. The prognosis may predict a probability of aggressiveness or metastasis of the cancer in the patient. Thus, detection of a measurable RHAMM expression in the sample may indicate a poor prognosis; and prescribing a course of treatment for the patient based on the prognosis.

In one aspect of the diagnostic and prognostic methods of the present invention, RHAMM expression in a sample may be compared to a known negative control or a known standard. Detection of a measurable RHAMM expression in the sample relative to the negative control or the known standard may be indicative of: presence of RHAMM in the sample, a diagnosis of cancer, or a poor prognosis, as the case may be.

FIGS. 6A, 6B, and 7 illustrate the visualization of human breast cancer cells using fluorescein-conjugated RHAMM-binding peptides SEQ ID NO: 14 (FIG. 6A; SEQ ID NO: 35) and SEQ ID NOs: 1 and 9 (FIG. 7; SEQ ID NOs: 25 and 29).

FIG. 13 illustrates the visualization of human ovarian cancer cells using fluorescein-conjugated RHAMM-binding peptides SEQ ID NO: 1 (SEQ ID NO: 25), while FIGS. 14A and 14B demonstrate the visualization of human prostate cancer cells using fluorescein-conjugated RHAMM-binding peptides SEQ ID NO: 9 (SEQ ID NO: 29).

As illustrated in FIGS. 14A and 14B, PC3mLN4 human prostate cancer lines, which are aggressively invasive and metastatic, are strongly positive for fluorescent staining indicating rapid uptake of the HA peptide mimetic SEQ ID NO: 9.

Cellular uptake of RHAMM-binding peptides of the present invention may be blocked by a specific anti-RHAMM mAb but not by a specific anti-CD44 mAb, which may however block binding of HA to CD44 (see FIGS. 6A, 6B, 7, 13, 14A and 14B). These results may indicate that the HA peptide mimetics of the present invention may associate with and may be taken up by prostate, breast and ovarian cancer cells by a RHAMM dependent mechanism.

2. Therapeutics

With reference to FIG. 9, the RHAMM-binding peptides of the present invention may have substantial stability in a biological environment (about 110 to about 250 minutes half-life), which may be long enough to facilitate their use in therapeutic methods.

The RHAMM-binding peptides of the invention may be used in the prophylaxis or treatment of pathological conditions involving cell locomotion such as cancer, inflammatory and autoimmune disorders, and fibrotic disorders associated with tissue trauma and its recovery in a mammal.

RHAMM-binding peptides of the present invention may be used in compositions and methods of treatment of disorders or conditions which may result from the formation of RHAMM/ligand complex by disrupting the formation of said RHAMM/ligand complex.

In one embodiment, the present invention may provide for a method for treating a subject who may be suffering from a disorder or condition associated with RHAMM expression in cells. The method may include at least administering to the subject an effective amount of a composition comprising an effective amount of one or more RHAMM-binding peptides or nucleic acids molecules encoding said one or more RHAMM-binding peptides and a pharmaceutically acceptable carrier.

In one embodiment, the present invention provides a method of preventing or reducing tissue scarring. The method may include at least administering an effective amount of one or more RHAMM binding peptide or nucleic acid molecules encoding said one or more RHAMM binding peptides of the invention to a subject in need thereof.

The ability of the RHAMM-binding peptides to inhibit the proliferation of cancer cells may implicate their effectiveness in preventing tumour metastasis and their utility as cancer chemotherapeutic agents. Accordingly, the present invention provides a method of preventing or reducing tumour metastasis comprising administering an effective amount of a RHAMM-binding peptide or a nucleic acid molecule encoding a RHAMM-binding peptide of the invention to a subject in need thereof.

As such, the RHAMM-binding peptides of the invention may be useful in treating cancers which may be associated with RHAMM expression including, without limitation, cancer of the lung, gastrointestinal, breast, bladder, skin cancer (melanoma and non-melanoma), brain, cervix, and leukemia. Accordingly, the present invention may provide a method of preventing or treating cancer in a subject. This method may include at least administering an effective amount of one or more RHAMM binding peptides or nucleic acid molecules encoding said one or more RHAMM binding peptides of this invention to a subject in need thereof.

In one embodiment, the RHAMM-binding peptides of the present invention may be used in combination with existing treatments to reduce morbidity and mortality in patients with a disorder or condition associated with RHAMM expression, such as cancer. Thus, in one embodiment of the present invention provided is a method for treating a subject for a disorder or condition associated with RHAMM expression. The method may include at least administering to the subject a RHAMM-binding peptide of the present invention in combination with at least one other therapy for said RHAMM-related disorder. The combination of the RHAMM-binding peptide and at lease one other therapy may increase the efficacy of the disease therapy. For example, in the case of cancer treatment, the subject may also be administered a therapy which may be capable of substantially reducing angiogenesis, such as small-molecule drugs, siRNAs, antisense therapy or any combinations thereof which may target one or more growth factors which may act as angiogenesis switches as well as providing proliferative signals for trophoblast and endothelial cells. Growth factors may be needed for the growth and survival of various cancers and may be essential for cancer progression. Therefore the anticancer methods of the invention using RHAMM-binding molecules may be combined with therapies targeted to one or more growth factors, including VEGF, FGR and hCG. The RHAMM-binding peptides of the present invention may also be combined with radiotherapy or chemotherapy. Such combination therapy contributes to a synergistic effect to treat cancer.

Figure 11:
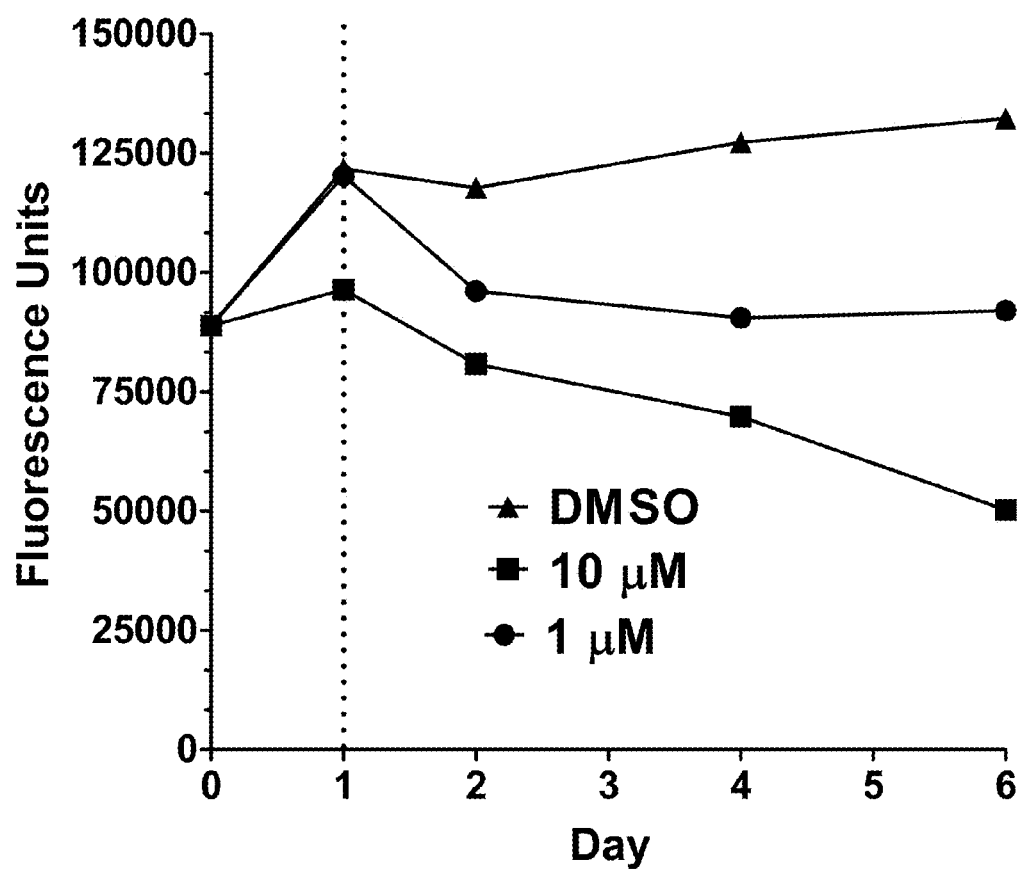
FIG. 11 is a graph illustrating a proliferation assay of human epithelial ovarian cancer (EOC) cells in the presence of different concentrations (1 µM and 10 µM) of RHAMM-binding peptide SEQ ID NO: 1. In this assay, cells were treated on day 1 and proliferation was followed for six days.

The inventors have shown, for example, that RHAMM-binding peptides of the present invention may be capable of inhibiting proliferation of human epithelial ovarian cancer (EOC) cells (see FIG. 11). The inventors have also shown that RHAMM-binding peptides of the present invention may be capable of reducing the viability of human EOC cells (see FIG. 12).

By identifying cancer progenitor cells as previously proposed, the detection methods of the present invention may allow for the development of novel therapeutics to selectively kill or force terminal differentiation of these progenitor cells. For example, the technology of the present invention may be used for in vivo imaging of tumors which may contain highly tumorigenic progenitor cell subsets, which may allow for selective treatment of patients at risk for metastasis vs. those not at risk. Most importantly, the technology of the present invention may be used to deliver anti-cancer drugs to the highly tumorigenic progenitor subsets present in primary cancers, such as breast cancers. For example, the peptide may be conjugated to a cytotoxic agent in order to enable the targeted delivery of the cytotoxic to the cells expressing RHAMM. By the same mechanism, the delivery of other therapeutic entities may be possible, including but not limited to, alkylating agents, anti-angiogenic agents, antimitotics, hormonal therapeutics, nucleoside analogues, or prodrugs thereof. Furthermore, radiotherapeutics may be envisioned whereby a RHAMM-binding peptide of the present invention may be linked to a particle emitting radionuclide thereby providing a mechanism of delivering a cell destructive entity selectively to the RHAMM positive cells. A therapeutic radionuclide can include a beta-emitting radionuclide such as $^{90}$Y, or $^{186}$Re; a beta/gamma emitting radionuclide such as $^{47}$Sc, $^{153}$Sm, $^{17}$Lu, or $^{188}$Re; alpha-emitting radionuclides such as $^{213}$Bi, $^{223}$Ra, or $^{225}$Ac; or Auger emitting radionuclides such as $^{67}$Ga or $^{111}$In.

3. Administration and Dosages

The probes and/or the peptides of the present invention may be administered directly to a mammalian subject using any route known in the art, including without limitation e.g., by injection (e.g., intravenous, intraperitoneal, subcutaneous, intramuscular, or intradermal), inhalation, transdermal application, rectal administration, intranasal or oral administration. In one embodiment, the detecting probes and/or peptides of the present invention may be administered subcutaneously. In another embodiment, the detecting probes and/or peptides of the present invention may be administered intravenously. In another embodiment, an effective amount of the probe or RHAMM-binding peptide may be administered via non-systemic, local administration, such as by peripheral administration which includes peripheral intramuscular, intraglandular, and subcutaneous administration routes, and allowing the probe and/or peptide several hours in vivo to be carried to sites having cells expressing RHAMM and tumorigenic cell populations.

Another embodiment of the present invention may be administering the RHAMM-binding peptides via an implantable device. In aspects of the invention, the implantable device may be capable of controlled release of the RHAMM-binding peptides.

The RHAMM-binding peptides of the present invention may be provided systemically as described herein above. As understood by one of skill in the art, the RHAMM-binding peptides of the invention may be used within conventional liposomes, specialized liposomes, lipid formulations and immunoliposomes.

The liposomes may be unilamellar or multilamellar and may be formed of constituents selected from phosphatidylcholine, dipalmitoylphosphatidylcholine, cholesterol, phosphatidylethanolamine, phosphatidylserine, demyristoyl-phosphatidylcholine and combinations thereof. The multilamellar liposomes may include multilamellar vesicles of similar composition to unilamellar vesicles, but may be prepared so as to result in a plurality of compartments in which the silver component in solution or emulsion is entrapped. Additionally, other adjuvants and modifiers may be included in the liposomal formulation such as polyethyleneglycol, or other materials.

While a formulation of liposome may include dipalmitoyl-phosphatidylcholine:cholesterol (1:1) it is understood by those skilled in the art that any number of liposome bilayer compositions may be used in the composition of the present invention. Liposomes may be prepared by a variety of known methods such as those disclosed in U.S. Pat. No. 4,235,871 and in RRC, Liposomes: A Practical Approach. IRL Press, Oxford, 1990, pages 33-101, which are hereby incorporated by reference.

The liposomes containing the RHAMM-binding peptides may have modifications such as having non-polymer molecules bound to the exterior of the liposome such as haptens, enzymes, antibodies or antibody fragments, cytokines and hormones and other small proteins, polypeptides or non-protein molecules which confer a desired enzymatic or surface recognition feature to the liposome. Surface molecules which preferentially target the liposome to specific organs or cell types include for example antibodies which target the liposomes to cells bearing specific antigens. Techniques for coupling such molecules are well known to those skilled in the art (see for example U.S. Pat. No. 4,762,915 the disclosure of which is incorporated herein by reference). Alternatively, or in conjunction, one skilled in the art would understand that any number of lipids bearing a positive or negative net charge may be used to alter the surface charge or surface charge density of the liposome membrane.

The liposomes may also incorporate thermal sensitive or pH sensitive lipids as a component of the lipid bilayer to provide controlled degradation of the lipid vesicle membrane.

The dose administered to a patient, in the context of the present invention may be a suitable dose to effectively image sites of RHAMM/RHAMM-binding ligand complexes and tumorigenic cell populations with sufficient specificity such that a surgeon may perform a biopsy or other procedure to remove tumorigenic cell populations detected by imaging RHAMM/RHAMM-binding peptide complexes. The dose may be determined by the efficacy of the particular vector (e.g. peptide or nucleic acid) employed and the condition of the patient, as well as the body weight or surface area of the patient to be treated. The size of the dose also may be determined by the existence, nature, and extent of any adverse side-effects that accompany the administration of a probe in a particular patient.

For administration, detecting probes of the present invention may be administered at a rate determined by the LD-50 of the polypeptide or nucleic acid, and the side-effects of the polypeptide or nucleic acid at various concentrations, as applied to the mass and overall health of the patient. Administration may be accomplished via single or divided doses, e.g., doses administered on a regular basis (e.g., daily) for a period of time (e.g., 2, 3, 4, 5, 6, days or 1-3 weeks or more).

In still further embodiments, about 5 to about 2000 LD 50 units of the labeled probe may be administered to said subject using recognized clinical standards and practices.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Blast Search and Sequence Alignment

A query sequence corresponding to the HA-binding domain (aa 718-750) of RHAMM (SEQ ID NO: 19) was used in basic search alignment search tool (BLAST) to compile a list of proteins which show sequence homologies. FIG. 1 B illustrates a flow chart of molecular imaging probe design and optimization. The HA-binding domain was used as the query sequence in BLAST to determine homologous protein sequences. Then, putative binding partners (ligands) for homologous sequences were elucidated. Library of peptides were synthesized based on truncation of ligand sequences and screened using surface plasmon resonance (SPR) binding assay to determine high affinity ligands. Candidate peptide ligands were then further evaluated using various in vitro binding assays.

Pair-wise comparisons between RHAMM and microtubule binding domain of MAPs and kinesins revealed moderate sequence homology (about 17%-24% as calculated using ClustalX2 [12]) to the HA binding domain of RHAMM; however, MAPs and RHAMM share similar physiochemical properties regarding the amino acid sequence of their tubulin binding site. In other words, both RHAMM and MAPs have a stretch of basic residues which are postulated to bind to tubulins. Furthermore, the secondary structures of the tubulin binding sites of MAPs and hyaluronan binding site of RHAMM has the same degree of helicity and both could be classified as a basic-zipper domain [13].

RHAMM has been reported to use a common binding site to associate with HA in the extracellular surface and microtubules in the cytosol [14]. Since microtubule-associated motor proteins and MAPs show direct binding to CTTs of tubulin, the inventors hypothesized that RHAMM could show direct interaction with synthetic peptides representing the CTTs of different tubulin subtypes. Since HA interacts with RHAMM mainly through ionic interactions between its negatively charged groups and the positively charged groups on RHAMM, molecules possessing an analogous distribution of negative charges can in principle serve as HA mimics. For instance, the Glu and Asp residues on tubulin CTTs may mimic the carboxylates on HA. Thus, the binding of synthetic CTTs to the HA binding domain of RHAMM might utilize the same charged side chains thought to be important for HA binding.

Example 2

Screening of Tubulin-Derived Peptides Against RHAMM

Materials: All solvents were used without further purification, and purchased from VWR, Fisher Scientific, or Sigma Aldrich. Fluorenylmethyloxycarbonyl (Fmoc)-Rink amide MBHA (100-200 mesh) resin, Fmoc amino acids, Fmoc-protected aminohexanoic acid (Fmoc-Ahx) and HBTU (2-(1H-benzotriazole 1-yl)-1,1,3,3-tetramethyluronium hexafluorophosphate) coupling reagent for peptide synthesis were obtained from Peptides International. N-(3-dimethylaminopropyl)-N'-ethylcarbodiimide hydrochloride (EDAC), N-hydroxysulfosuccinimide sodium salt (sulfo-NHS), fluorescein isothiocyanate (FITC) isomer I and fetal bovine serum (FBS) were purchased from Sigma Aldrich. NHS-Biotin was obtained from Nova BioChem. Antibodies such as anti-RHAMM (Santa Cruz Biotechnology, USA), anti-CD44 (Pharmigen) and IgG ab (Santa Cruz Biotechnology USA) were obtained commercially.

Peptide Synthesis: Seventeen (17) peptides having 12 amino acid residues corresponding to the CTT and H12 region of different tubulin subtypes were synthesized using solid-phase peptide synthesis following Fmoc protocols.

Elongation of peptide chains on rink amide MBHA resins (0.1 mmol) was performed using automated (APEX 396 auto-synthesizer) and/or manual methods using standard solid phase peptide synthesis involving Fmoc deprotection and amino acid coupling cycles, and each cycle was monitored using Kaiser test [15, 16]. Repeated Fmoc deprotection throughout the synthesis (15 and 20 minutes periods) was carried out using 20% piperidine solution in N,N-dimethylformide (DMF). All amino acid couplings were carried out using 0.05 M or higher concentration of Fmoc-protected amino acid and HBTU, 5 equivalent of N,N-diisopropylethylamine (DIPEA) in DMF at 30 and 90 minutes intervals. After each deprotection and coupling step, the resin was washed repeatedly with DMF (3×) and dichloromethane (DCM) (3×). Fmoc-Ahx was coupled using the same parameters. Acylation of the amino terminus was done (15 and 10 minutes) using 10% acetic anhydride in DMF following Fmoc deprotection. Fluorescein coupling was carried out by reacting the amino group of the peptide with FITC fluorescent dye (4 equiv.) in DMF with DIPEA (2 equiv.) for 4 hours.

Full deprotection of cysteine-containing peptides was accomplished using a solution of 94% v/v trifluoroacetic acid (TFA), 1% v/v triisopropylsilane (TIPS), 2.5% v/v $H_2O$ and 2.5% v/v 1,2-ethanedithiol (EDT) for 1.0-1.5 hours. Full deprotection of all other peptides was done using a solution of 88% v/v TFA, 5% v/v water, 5% m/v phenol, 2% v/v TIPS for 2-4 hours. The filtrate was collected, precipitated using cold tert-butyl methyl ether and pelleted via centrifugation at 3000 rpm in −5° C. for 10 minutes. Pellets were then dissolved in distilled-deionized water and lyophilized yielding solid powders.

Protein Purification: All peptides used in this study were purified to greater than 92% purity by reverse-phase HPLC and characterized by ESI mass spectrometry.

Purification of peptides was performed using gradient solvent system consisting of $H_2O$+0.1% TFA (solvent A) and $CH_3CN$+0.1% TFA (solvent B) at a linear flow rate of 1.5 mL/min and 20 mL/min for analytical and preparative HPLC, respectively. Analytical HPLC was performed using a Grace Vydac Protein/Peptide RP-C18 column (4.6 mm×250 µm, 5 µm), and preparative HPLC was performed using a Grace Vydac protein/peptide RP-C18 column (22.0 mm×250 mm, 10 µm). Absorbance was detected at wavelengths of 220 nm and 254 nm using a Waters 2998 Photodiode Array detector. During purification, fractions were collected, lyophilized, and analyzed by ESI-MS (Waters Micromass Quattro Micro™ API).

Recombinant protein RHAMM-CT (a truncated RHAMM corresponding only to the carboxy terminus which contains the HA binding domain, amino acids 706-766, sequence: RDSYAQLLGH QNLKQKIKHV VKLKDENSQL KSEVSKLRSQ LVKRKQNELR LQGELDKALG I, M.W. 7.1 kDa, pI=10.1; SEQ ID NO: 20) was isolated from *E. coli* BL21 (D3) strain carrying the recombinant plasmid pPAL7-RHAMM. Bacteria were grown overnight in LB medium at 37° C. containing ampicillin (100 µg/ml) and 0.5% glucose, and allowed to grow to mid-log phase. Recombinant RHAMM gene expression was induced with 2 mM IPTG for 4 h at 37° C. and bacterial cells were harvested by centrifugation at 10,000×g for 20 min. Bacterial cells were re-suspended in lysis buffer (composed of 0.2 M sodium phosphate, 0.2 M potassium acetate, 1% triton X-100, and 0.1% protease inhibitors, pH=7.0), sonicated (60 s, 10 s/pulse), and centrifuged (4° C., 12000×g, 20 min). The resulting supernatant was transferred to a clean tube and filtered (using 0.45 µm filter). Purification of the eXact tagged-recombinant RHAMM were conducted with Profinity eXact (Bio-Rad, USA) affinity resin according to manufacturer's protocol. For this experiment, the lysate was loaded to gravity column packed with Profinity eXact affinity resin (4 mL resin, column 15×1.5 cm) equilibrated with wash buffer (0.2M sodium phosphate, pH=7.0). The column was washed with wash buffer to eliminate impurities, and recombinant RHAMM was eluted with elution buffer (composed of 0.2M sodium phosphate, 0.1M sodium fluoride, pH=7.0). Then the protein was dialyzed and concentrated, using Millipore Filter (Millipore, USA, cut-off 3 kDa) in a buffer consisting of 0.2M sodium phosphate, and 0.2 M potassium acetate (pH=7.0). The purity of the isolated protein was verified on 1D SDS-PAGE. Identification of RHAMM was performed and confirmed with anti-RHAMM antibody by Western blot analysis.

SPR (Surface Plasmon Resonance) Screening Assay: ProteON XPR36 system was used for the selection and ranking of different tubulin derived peptides against RHAMM. For immobilization of RHAMM, the ProteON GLC sensor chip surfaces were activated by amine coupling using 100 mM EDAC and 24 mM sulfo-NHS. RHAMM (30 µg/mL in sodium bicarbonate buffer, pH 9.7) was injected at a flow a rate of 30 µl/min. A buffer sample was injected on a different sensor plate for use as a reference. Ethanolamine HCl (1M, pH 8.5) was then injected to deactivate any remaining surface groups. Peptides (10 µM in PBS-T, 2% DMSO) were injected to a RHAMM functionalized surface at 50 µL/min for 3 minutes followed by a 10 minute dissociation (i.e. injection of PBS-T buffer) period. The surfaces were regenerated using two injections of 30 µL of 1M NaCl prior to the injection of the next peptide. In all experiments, reference subtraction was performed using data obtained from reference plate (No RHAMM) and RHAMM functionalized plate.

Competitive ELISA experiments using fluorescein-labelled peptides: ELISA was carried out to test the ability of FITC-labelled tubulin-derived peptides compete with HA for binding site with RHAMM. Recombinant RHAMM (100 µL, 10 µg/mL in 0.05M PBS, pH=9) was immobilized on 96-well ELISA plates (final concentration of 1 µg/well) and incubated overnight at 4° C. resulting in final amount of protein 1 µg/well. Plates were washed three times with (0.05%) PBS-Tween-20 buffer (200 µL/well), washed with blocking buffer (5% 200 µL/well, PBS-Tween-20 per well), and incubated for 1 hour at room temperature. Following three washes as described above, FITC-labeled tubulin derived peptides (final concentration of 1 µg/mL) and HA (100 µL/well, M.W. 220 kDa, 10 µg/mL in PBS, serial dilutions have been made for HA=1:1, 1:2, 1:4, 1:8, 1:16) were added to plates and incubated overnight at 4° C. Plates were washed as described above, and absorbance was measured at 485/535 nm.

Competitive ELISA experiments using fluorescein-labelled RHAMM: ELISA was carried out to test the ability of non-labeled tubulin-derived peptides to compete with dye (Alexa Fluor 647)-conjugated HA for RHAMM. RHAMM (100 µl, 10 µg/ml in 0.05 M PBS, pH=9) was immobilized on 96-well ELISA plates (to achieve a final amount of 1 µg/well) and incubated overnight at 4° C. Plates were washed three times with (0.05%) PBS-Tween-20 buffer (200 µl/well), then incubated with blocking buffer (200 µl/well, 5% Tween-20 in PBS) for 1 hour at room temperature. Following three washes of (0.05%) PBS-Tween-20 buffer, tubulin-derived peptides (10 µg/ml) and HA-conjugated Alexa Fluor 647 (100 µl/well, M.W. 220 kDa, 10 µg/ml in PBS) were added to plates and incubated overnight at 4° C. Negative control plates receive no dye-conjugated HA and all experiments were done in triplicate. Plates were washed as described above and the fluorescence was measured at 650 nm.

SPR (Surface Plasmon Resonance) Binding Assay: After peptide screening, GWC SPRimager®II system was used to determine binding kinetic constants. Thiol-containing peptides at 1 nM concentration in milliQ water were immobilized on a maleimide-functionalized gold-plated chip for 3 hours. Excess peptides were removed by washing with milliQ water. For binding studies, a series of concentrations (500 nM, 750 nM, and 1000 nM) of RHAMM were injected over the immobilized peptides. After a 15 min dissociation phase, the sensor chip surface was regenerated for the next peptide sample injection, via treatment with two 10 min pulse injections of regenerating buffer (2 M NaCl in HBS-EP, pH 7.4) at 100 mL/min. Baseline returned to the initial value after the regeneration step, confirming the removal of all bound analytes. Data were analyzed and the corresponding dissociation constants ($K_D$) were obtained via non-linear regression fitting to a Langmuir binding model [17]. In all experiments, reference subtraction was performed using data obtained from reference plate (no peptide) and peptide functionalized plate.

Serum Stability Study The stability of tubulin CTTs in serum was evaluated for up to 11 hours. Each peptides were mixed with pre-heated (37° C., pH 7.3±0.1) fetal bovine serum (FBS), (final sample volume of 3 mL and peptide concentration of 15 µM). The initial time is recorded, and at each 30 minute time point, 40 µL aliquots were taken from the reaction mixture and passed through C18 reverse-phase (C18 Sep-Pak©) cartridge. Peptides were eluted from the cartridge using 3 mL ethanol (70% v/v) with 0.1% TFA, lyophilized, and analyzed using analytical RP-HPLC (Grace Vydac Protein/Peptide RP-C18 column 4.6×250 mm, 5 µm). Employed mobile phase of this system were 0.1% TFA in water (eluent A) and 0.1% TFA in $CH_3CN$ (eluent B). Linear gradient of 10-95% of eluent B at a flow rate of 1.5 ml/min over 20 minutes was used for each peptide sample. Percent intact peptides were detected using Waters 2998 Photodiode array detector set at 220 and 254 nm, and identified using ESI-MS. Half-life of peptides were determined using GraphPad Prism version 5.01.

Cell Uptake Studies: Candidate peptides showing high affinity for RHAMM-CT were conjugated to a fluorescent dye (FITC) and their specificities for RHAMM expressing cancer cells (MDA-MB-231) were evaluated using a cellular fluorescence imaging assay.

MDA-MB-231 cells cultured in DMEM media and 10% FBS up to 90% cofluency. Then the cells were seeded on a glass cover slip (12×12 mm, coated with 50 ug/ml fibronectin) in a 2×24-well tissue culture place (confluency of 20000/well) one day after seeding. Starvation step carried out with DMEM+0.1% FCS overnight at 37° C. Then culture medium was aspirated, and was rinsed with DMEM+0.1% FCS overnight at 37° C. Cells were blocked with 3% BSA in DMEM+0.1% FCS for 1 hour at room temperature. For blocking experiments, antibodies (dilution 1:100, mouse IgG ab, goat, anti-RHAMM mAb, or mouse anti-CD44 mAb in DMEM+0.1% FCS media) were added and incubated at 37° C. for 1 hour. Cells blocked with anti-mouse IgG serve as positive control since the antibody shows no binding affinity to RHAMM.

Then the resulting culture medium was aspirated, and cells were washed with DMEM+0.1% FCS at RT. Fluorescein-conjugated peptides (50 µg/ml) were added and incubated at 37° C. for 30 minutes. Cells were washed with DMEM+0.1% FCS, then with PBS (pH=7.6). Then cells were mounted using Fluoro-gel 11 containing DAPI (Electron microscopy sciences, USA) via manufacturer's protocol. Cells were photographed using Olympus FluoView FV1000 coupled IX81 Motorized Inverted System Microscope. Tiff images were analyzed using ImageJ (v1.42q) software. Each image was converted to an 8-bit format and subjected to threshold values of 20 and 255. Regions of interest (ROI) corresponding to cell bodies (n=15) were selected. Mean fluorescence of each ROI was then calculated using 8-bit acquired data. Data were analyzed using Prism (GraphPad Software, San Diego, USA) statistical program for one-way ANOVA.

Results

Figure 2:
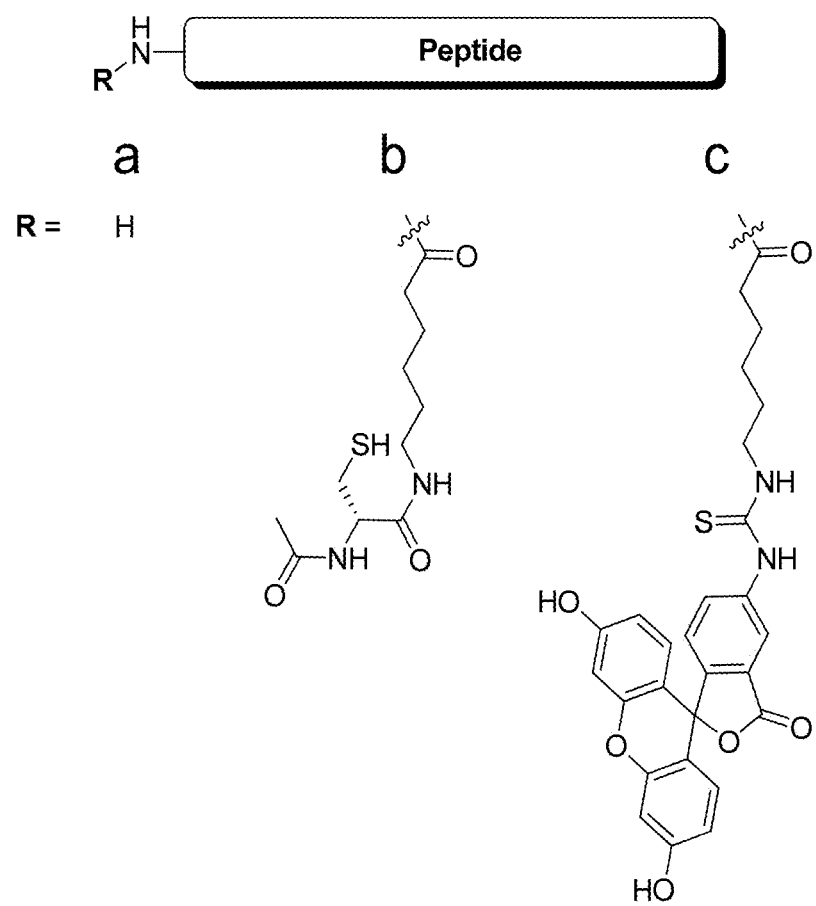
FIG. 2 A illustrate the general structure of (a) unmodified tubulin-derived peptides, (b) tubulin-derived peptides conjugated to N-acetyl cysteine, and (c) tubulin-derived peptides conjugated to fluorescein isothiocyanate.

Screening of Tubulin-Derived Peptides Against RHAMM:

FIG. 2 A shows the general structure of unmodified tubulin-derived peptides (FIG. 2 A a), as well as peptides conjugated to N-acetyl cysteine (FIG. 2 A b) and fluorescein isothiocyanate (FIG. 2 A c). FIGS. 2 B and 2 C provide a table which describes all 17 peptides prepared for this study. Sequences of 17 synthesized peptides encompass the CTTs of different tubulin subtypes as well as sequences directly flanking α1a- (SEQ ID NOs: 6, 7 and 8) and βIIIa-CTT (SEQ ID NOs: 13 and 14). A six carbon linker was used to increase the distance between the peptide and an additional peptide modification. FIGS. 2 B and 2 C also include derivatized peptides. Derivatized peptides were prepared with either fluorescein (peptides 1c, 3c, 9c, 11c, 12c, 14c of FIGS. 2B and 2C; SEQ ID NOs: 25, 27, 29, 31, 33 and 35) or N-acetyl cysteine modified N-terminus (peptides 1b, 3b, 9b, 11 b, 12b, 14b of FIGS. 2B and 2C; SEQ ID NOs: 24, 26, 28, 30, 32 and 34).

All peptides were characterized by ESI+ mass spectrometry and analyzed for purity by reverse-phase HPLC. FIGS. 2 B and 2 C provide a table illustrating the analysis of the 17 synthesized tubulin-derived peptides using ESI-MS and RP HPLC. The calculated and observed m/z values are based on the prominent observed signals as determined by ESI. Percent purity determined by RP HPLC with detection at 220 nm.

A SPR (surface plasmon resonance)-based screening method was utilized for rapid and accurate determination of potential peptide candidates that are able to recognize the HA-binding domain of RHAMM. Seventeen tubulin-derived peptides were screened, and the resulting sensograms were used to deduce peptides which show affinity to RHAMM. Prior to screening, the optimal condition for ligand immobilization, in this instance RHAMM, to the sensor plate was determined. The optimal pH for the immobilization buffer balances the electrostatic attraction of the protein to the sensor plate while minimizing protein deactivation. In this study the optimal pH for immobilization was determined to be the pH that yielded the highest ligand density. RHAMM was coupled to the sensor plate using sodium bicarbonate buffer of varying pH, at a flow rate of 30 μL/min and with fixed concentration of EDAC and sulfo-NHS. The RHAMM ligand density for each pH immobilization condition was determined from the average SPR response of six measurements and the maximum ligand immobilization occurred at pH 9.7 (FIG. 3 A). Ligand immobilization was slightly lower than pH 10.1 due in part to loss of net charge on RHAMM at its isoelectric point.

After immobilization of RHAMM on the SPR sensor chip, injection of a series of tubulin derived peptides was carried out. Association of the peptides with RHAMM proceeded for 3 minutes and the dissociation in analyte free buffer was carried out for 10 minutes. FIG. 3 B shows the experimental sensograms obtained at a concentration of 10 μM. For each peptide injection, control sensograms (no immobilized RHAMM and buffer injection) were subtracted from the test sensograms, and the chip surface was regenerated prior to the next peptide injection in order to remove any remaining bound peptides. Screening of 17 peptides resulted in six peptides demonstrating enhanced affinity to RHAMM, namely: 1a (SEQ ID NO: 1), 3a (SEQ ID NO: 3), 9a (SEQ ID NO: 9), 11a (SEQ ID NO: 11), 12a (SEQ ID NO: 12), and 14a (SEQ ID NO: 14).

Figure 4:
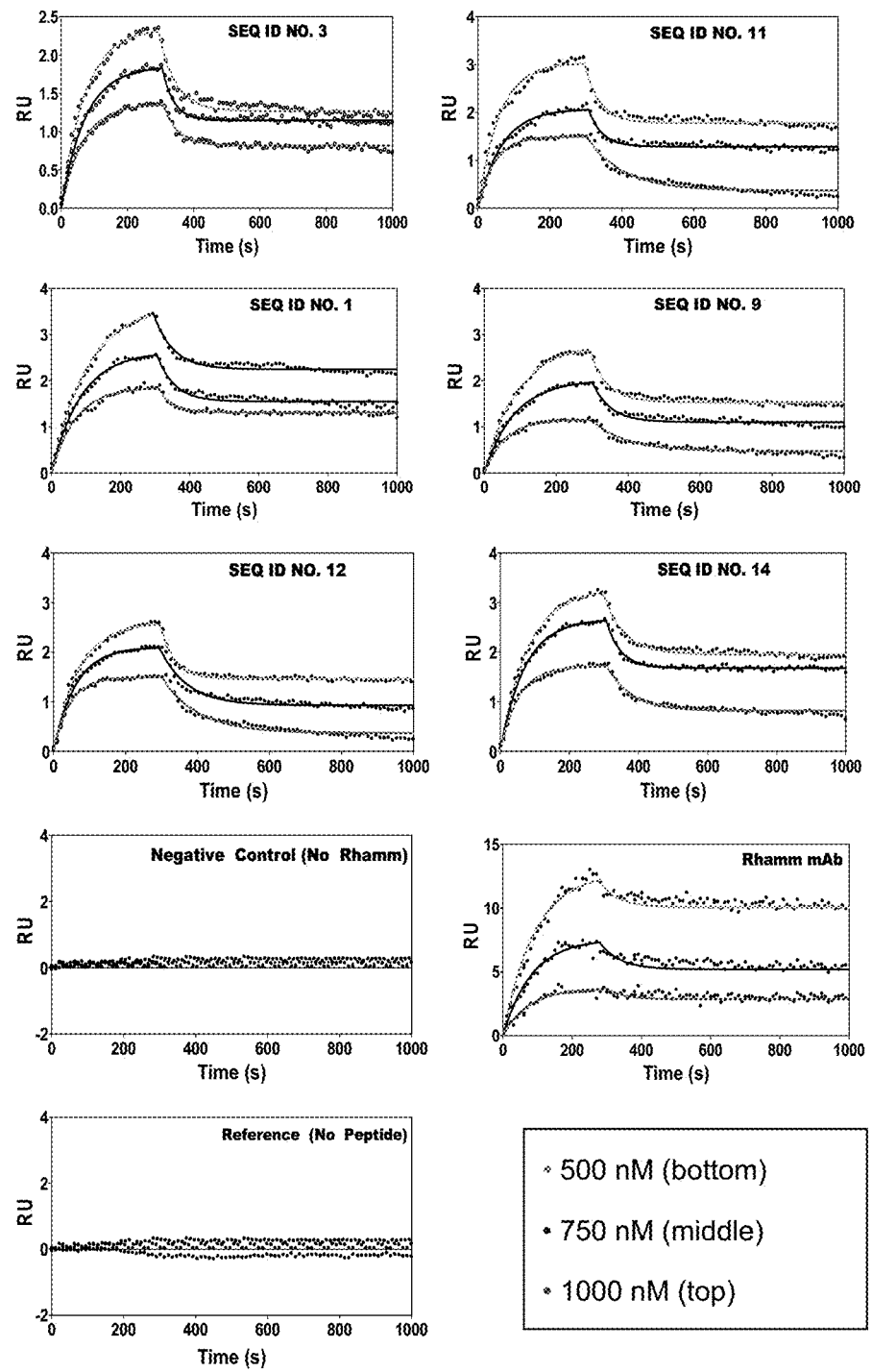
FIG. 4 A illustrates seven sets of sensograms showing global fits to each specific peptide-RHAMM interaction, with negative control and reference sensogram plot. Anti-RHAMM mAb was used as a positive control. Each set of sensogram corresponds to the responses of three RHAMM concentrations (1000 nM, 750 nM and 500 nM) interacting with immobilized peptide.

Affinity of Immobilized Tubulin Derived Peptides to RHAMM: The binding of the six peptides deduced in the previous section to RHAMM was quantified. Truncation studies indicate that the CTTs (i.e. the last 12 carboxy-terminal residues of S-peptides), were sufficient to induce MAP-directed microtubule assembly [18], thus placing a label spaced by a linker moiety on the amino terminus of CTT should not affect the peptide-protein interaction. Peptides were immobilized on the sensor plate and RHAMM was flowed over derivatized surface at different concentrations at a constant flow rate of 100 μL/min. FIG. 4 A depicts the resulting sensograms. Again, each sensograms has been corrected by subtracting each curve from a reference sensorgram (data acquired from the sensorgram without immobilized peptide) in order to account for refractive index differences between running buffer and sample solutions.

Experimental sensograms were fitted with curves resulting from a kinetic model for a 1:1 Langmuir binding model. The average values for $K_D$ of the 6 peptides obtained from different RHAMM concentrations are given in the table of FIG. 4 B together with the respective standard errors. As a positive control, the kinetic profile of anti-RHAMM mAb was also measured and results show 5.53 nM affinity to RHAMM. Peptides SEQ ID NO: 1 ($K_D$=24 nM), SEQ ID NO: 9 ($K_D$=32 nM), and SEQ ID NO: 14 ($K_D$=30 nM) showed dissociation constants in the low nanomolar range indicating high affinity to RHAMM.

The relative binding affinities of each of the 6 peptides were also measured using ELISA. In this assay, peptides were labelled with fluorescein, with the dye situated away from the peptide by the addition of an aminohexanoic acid linker. As shown in FIG. 3 C ELISA results also indicated that peptides SEQ ID NOs: 1, 9 and 14 had the highest relative binding affinity in all concentrations. It may be possible that the fluorophore modification to the peptide could have an effect on the ligand-RHAMM interaction or on non-specific binding, thus SPR and ELISA results might not exactly match.

Figure 5A:
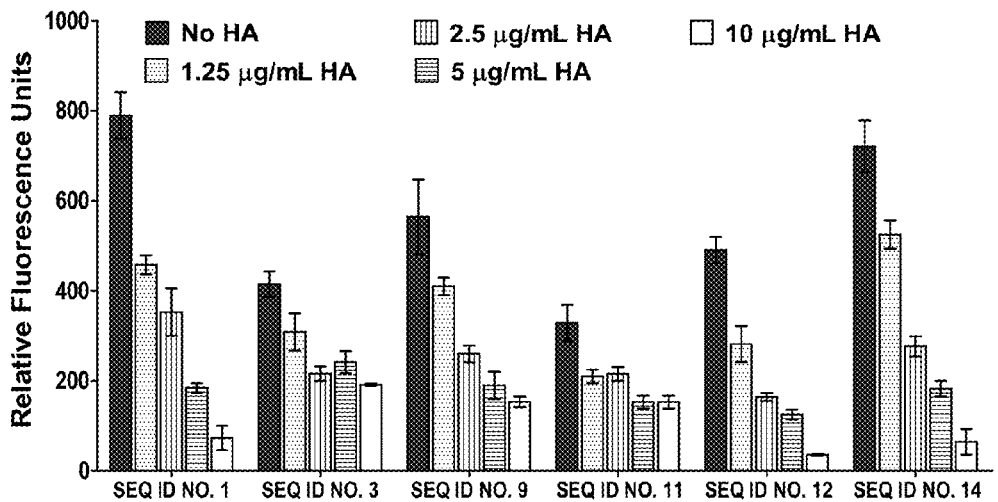
FIG. 5 A is a graph which shows competitive displacement of six selected fluorescein-labelled RHAMM-binding peptides SEQ ID NOs: 1, 3, 9, 11, 12 and 14 (corresponding to SEQ ID NOs: 25, 27, 29, 31, 33 and 35 respectively) of the present invention by HA (0, 1.25, 2.5, 5, and 10 μg/mL) to immobilized RHAMM-CT. Data shows mean of three measurements in two independent experiments.
Figure 5B:
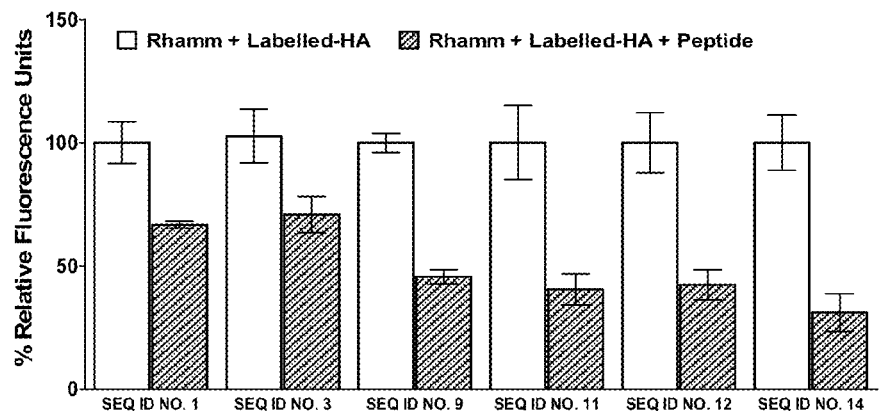
Figure 5C:
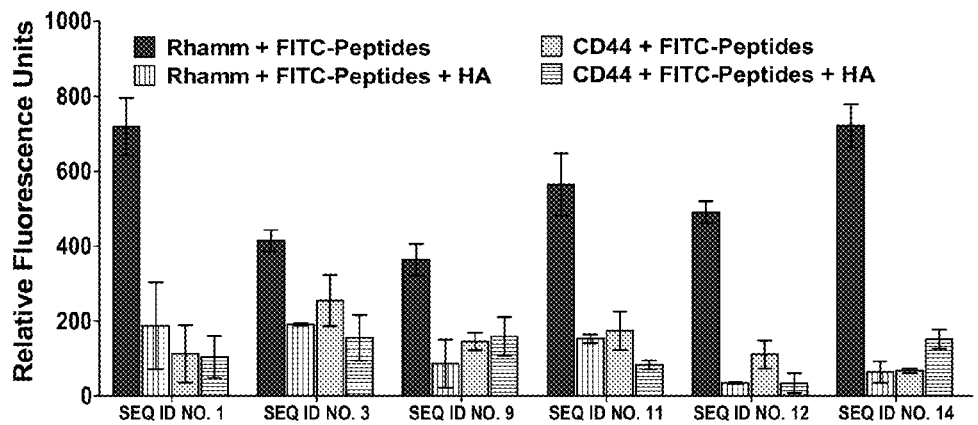

Competitive displacement of tubulin-derived peptides by HA: A competitive ELISA was done to determine the selectivity of the peptides to the HA binding domain of RHAMM. In this assay, fluorescein-labelled peptides were used and the effectiveness of unlabelled HA to block the binding of peptides to RHAMM was evaluated. Fluorescein-labelled peptides SEQ ID NOs: 1, 3, 9, 11, 12 and 14, corresponding to peptides 1c, 3c, 9c, 11c, 12c and 14c in FIGS. 2B and 2C (SEQ ID NOs: 25, 27, 29, 31, 33 and 35) were added to ELISA plates containing immobilized RHAMM, followed by the addition of varying concentration of HA, which is the natural ligand of RHAMM. A decrease in observed fluorescence is seen as HA displaces the fluorescein-labelled peptides if they compete for the same binding site. FIG. 5 A shows competitive displacement of peptide binding to RHAMM by HA, and a concentration dependent decrease in fluorescence is observed for all six ligands as the HA competitor concentration increases, with the most effective relative displacement occurring for fluorescein-labelled peptides SEQ ID NOs: 1, 12 and 14 (SEQ ID NOs: 25, 33 and 35), although peptide of SEQ ID NO: 9 (SEQ ID NO: 29) was also displaced.

An alternative competition experiment was devised to further assess the peptide ligands since the presence of the fluorescein label may influence the physical properties of these low molecular weight peptides and the resulting binding potential. Using ELISA, unlabelled peptides SEQ ID NOs: 1, 3, 9, 11, 12 and 14 (corresponding to peptides 1a, 3a, 9a, 11a, 12a and 14a of FIGS. 2B and 2C) were used to compete with dye-labelled HA. This assay eliminates confounding results arising from the interaction between the dye label and protein or a change in affinity caused by the addition of a bulky dye to the peptide ligand. As shown in FIG. 5B, displacement of labelled-HA by non-fluorescent peptides derived from tubulin is readily observed by decrease of the fluorescence signal. Unlabelled RHAMM ligand or fluorescein-labelled ligand SEQ ID NO: 14 and unlabelled RHAMM ligand or fluorescein-labelled ligand SEQ ID NO: 9 appear especially able to compete for the binding with HA consistently, thus reinforcing the notion that further modification at the amino terminus of the peptide has little effect on the binding to RHAMM. However, fluorescein-labelled αla-CTT (peptide 1c; SEQ ID NO: 25), which contains the sequence SEQ ID NO: 1, seemed better at competing with HA compared to unmodified peptide of SEQ ID NO: 1.

Specificity for RHAMM versus CD44: The previous results indicate that these peptides may be able to target the HA binding domain of RHAMM. However to show these HA mimics are specifically targeting RHAMM, it is necessary to test the affinity of the peptides to other hyaladerins such as CD44. To this end, a solid phase peptide binding assay (ELISA) was performed with a CD44 functionalized surface, which is illustrated in FIG. 5 C. As described above, each FITC-conjugated peptide of SEQ ID NOs: 1, 3, 9, 11, 12 and 14 (SEQ ID NOs: 25, 27, 29, 31, 33 and 35) was incubated to each hyaladerin (RHAMM or CD44) and the resulting fluorescence measurement was recorded following extensive washing protocols. As expected, fluorescence measurement arising from RHAMM and fluorescein-peptides showed the highest signals, and a remarkable drop in fluorescence was observed following the addition of HA. Conversely, CD44 and fluorescein-peptide interaction, as indicated by fluorescence, is significantly lower and fails to show the expected decrease in fluorescence measurement following the addition of HA. Thus, the binding of the peptides is caused by a specific interaction with RHAMM, while they show limited interaction with CD44.

Serum Stability: To test their potential as targeting entities or therapeutics, the stability of the RHAMM-binding peptides in biological environments needs to be investigated. In vitro serum stability of each of peptides SEQ ID NOs: 1, 3, 9, 11, 12 and 14 was evaluated over a period of 11 hours, and the quantification of remaining intact peptide was deduced using RP-HPLC. In this assay, the peptides are subjected to fetal bovine serum at 37° C., and aliquots were taken at 30 minutes intervals. At each time point, the reaction was stopped by precipitating serum protein with trifluoroacetic acid (TFA), and centrifugation was used to obtain a crude solution containing the peptides. The solution was passed through a C18 reverse-phase column (C18 Sep-Pak©) to eliminate low molecular weight impurities. Intact peptides were eluted from the column, lyophilized, and analyzed. As shown in FIG. 9 unmodified RHAMM-binding peptides showed serum stability with a reasonable half-life of approximately 2-4 hours.

Cellular fluorescence assay (MDA-MB-231 Uptake Studies): To determine the specificity of tubulin derived peptides of the present invention to RHAMM expressing cells and their potential as a targeting entity, a cellular fluorescence assay was performed using MDA-MB-231 cells treated with anti-RHAMM antibody. MDA-MB-231 breast tumour cell line shows high expression of RHAMM receptors, thus this cell line was an ideal choice for evaluation of the targeting and specificity of synthetic tubulin peptides. MDA-MB-231 cells were incubated with fluorescein-conjugated peptides SEQ ID NOs: 1, 9 and 14 (SEQ ID NOs: 25, 29 and 35) and cellular uptake of the probe was measured. As illustrated in FIG. 6A (for SEQ ID NO: 35) and FIG. 7 (for SEQ ID NOs: 25 and 29) for all tested peptides accumulation of fluorescence signal was observed in cells which receive no blocking treatment and also in cells incubated with non-specific antibody (IgG antibody), indicating high uptake of fluorescein-labelled probe. Interestingly, cells blocked with anti-CD44 showed no reduction of signal. However, cells blocked with anti-RHAMM mAb showed significant decrease in cellular fluorescence confirming the specificity of peptides SEQ ID NOs: 1, 9 and 14 to RHAMM ($p<0.001$). As illustrated in FIG. 6 B, cells blocked with anti-RHAMM mAb showed about 65% to about 85% reduction in cellular fluorescence (fluorescein-labelled SEQ ID NOs: 1, 9 and 14 showed about 85%, about 76% and about 65% reduction in fluorescence, respectively).

Discussion

RHAMM is an oncogene that is over-expressed in a variety of cancers. In addition, increased accumulation of HA, the extracellular ligand of RHAMM, within RHAMM-expressing cancer cells is a prognostic factor for poor clinical outcome. Thus, low molecular weight ligands targeting RHAMM that are able to compete with HA for binding may be useful for diagnostic and therapeutic purposes. In this study, the inventors sought to identify ligands that could target the HA binding domain of RHAMM. The inventors reasoned that since the carboxy-terminus of RHAMM, which contains the HA binding domain, mediates the localization at the microtubule network within the cell, database searches and pairwise comparison between RHAMM and microtubule binding domain of known tubulin associated proteins (e.g. MAPs) were performed. Furthermore, since these proteins show direct binding to CTTs of tubulin, the inventors hypothesize that RHAMM may show direct interaction with synthetic peptides representing the CTTs of different tubulin subtypes. Due to moderate homology between the tubulin binding domain of MAPs and HA-binding domain of RHAMM, further investigation was performed to determine which peptide fragments of tubulin interacts with RHAMM. In this study, the specific interaction between RHAMM and novel ligands were deduced.

Peptide fragments derived from the carboxy terminal domain of different tubulin subtypes (i.e. CTT region), as well as sequences directly adjacent to the aforementioned domain, were synthesized using solid-phase peptide synthesis. The resulting peptides were screened against RHAMM to determine high affinity ligands. To this end, an SPR screening method was utilized, wherein, RHAMM protein was immobilized to the SPR sensor plate, and peptides were flowed to discover ligands with high affinity and specificity. This method was utilized because it allows for high throughput screening using a single RHAMM-charged sensor plate and the SPR-bound RHAMM could reflect its native membrane bound state as a cellular receptor. The screening afforded six high-affinity ligands that are able to compete with HA for the HA binding region of RHAMM as determined by ELISA. Further evaluation determined that these peptides showed a higher specificity to RHAMM compared to CD44, a known hyaladerin that also binds HA.

Peptides showed moderate stability (approximately 110-250 minutes half-life) in a biological environment (bovine serum), which may be long enough to facilitate in vitro, ex vivo or in vivo imaging. The specificity of the three HA peptide mimics (SEQ ID NOs.: 1, 9 and 14) showing the higher affinity for RHAMM was analyzed by quantifying the relative uptake of the ligands in RHAMM-expressing cancer cells. To this end, peptides of SEQ ID NOs.: 1, 9 and 14 were conjugated with fluorescein (SEQ ID NOs: 25, 29 and 35) and incubated with MDA-MB-231 cells, a cell line which over-expresses RHAMM. Cellular fluorescence was observed for all three peptides and uptake was not diminished by the addition of anti-CD44 or non-specific antibodies (i.e. IgG antibodies). However, dramatic decrease in probe uptake as observed upon the addition of anti-RHAMM antibodies suggesting specific blocking of probe uptake. Thus, the high specificity of the probes combined with moderate stability may allow for further development as diagnostic agents for RHAMM-expressing cancer cells.

The described results shown in this report suggest the presence of a common site for the HA binding domain of RHAMM at the variable carboxy-terminal moieties of tubulin. A recurring hexapeptide motif was noted in most peptide candidates, and peptides sharing this acidic carboxy-terminal segment interacted with RHAMM. The motif, EEXEEZ (where X is A or G, and Z is Y or E; SEQ ID NO: 18), is present in synthetic αIa (SEQ ID NO: 1), αIIIc (SEQ ID NO: 3), βIa (SEQ ID NO: 9), and βIV-CTT (SEQ ID NO: 11) as illustrated in FIG. 8B. The present results are in agreement with the previous reports that the short sequence EEGEE (SEQ ID NO: 21) (Paschal et al., 1989) could be involved in tubulin and MAP binding, a family of proteins which shares sequence homology to RHAMM.

Despite the role of acidic functional groups in HA and RHAMM interaction, results may also suggest that the random occurrence or an increase of these acidic residues within the CTT region does not appear to be directly influencing the RHAMM-tubulin interaction. It is surprising that peptides containing DEXEEZ (as seen in peptides SEQ ID NOs: 2 and 4) (SEQ ID NO: 22) and EEXEDZ (as seen in SEQ ID NO: 10) (SEQ ID NO: 23) motifs failed the initial screening, suggesting that Asp residues within the first and fifth sequence cannot substitute a similar acidic Glu residue within this motif. This suggests that the CTT interaction with RHAMM is mediated by both electrostatic forces and conformational effects.

Significance

This study discloses the discovery of at least six novel ligands that interact with the HA binding domain of RHAMM. These six peptides showed strong affinity to RHAMM and were able to be displaced by endogenous HA, thus demonstrating the specific targeting to the HA-binding domain. In addition, the greater propensity of these ligands to bind to RHAMM as compared to another hyaladerin CD44, both in non-cell based (i.e. ELISA) and cell based (i.e. cellular fluorescence) assays, may demonstrate their potential as a targeting entity. The over-expression of RHAMM and its resulting interaction with HA has been implicated in the pathology of cancers. Therefore, these peptides may serve as antagonists that could block the RHAMM-HA interaction, thus limiting the transforming potential of RHAMM.

Example 3

Affinity of Alanine-Substituted RHAMM-Binding Peptides to RHAMM

Materials: Solvents were used without further purification, and purchased from VWR, Fisher Scientific, or Sigma Aldrich. Fluorenylmethyloxycarbonyl (Fmoc)-Rink amide MBHA (100-200 mesh) resin, Fmoc amino acids, Fmoc-protected aminohexanoic acid (Fmoc-Ahx) and HBTU (2-(1H-benzotriazole 1-yl)-1,1,3,3-tetramethyluronium hexafluorophosphate) coupling reagent for peptide synthesis were obtained from Peptides International.

Peptide Synthesis: Elongation of peptide chains on rink amide MBHA resins (0.1 mmol) was performed using automated (APEX 396 auto-synthesizer) and/or manual methods using standard solid phase peptide synthesis involving Fmoc deprotection and amino acid coupling cycles. Repeated Fmoc deprotection throughout the synthesis (15 and 20 minutes periods) was carried out using 20% piperidine solution in N,N-dimethylformide (DMF). All amino acid couplings were carried out using 0.05 M or higher concentration of Fmoc-protected amino acid and HBTU, 5 equivalent of N,N-diisopropylethylamine (DIPEA) in DMF at 30 and 90 minutes intervals. After each deprotection and coupling step, the resin was washed repeatedly with DMF (3×) and dichloromethane (DCM) (3×). Fmoc-Ahx was coupled using the same parameters. Fluorescein coupling was carried out by reacting the amino group of the peptide with FITC fluorescent dye (4 equiv.) in DMF with DIPEA (2 equiv.) for 4 hours. The ensuing resin was treated with cleavage cocktail consisting of 88% TFA and 12% scavengers (5% water, 5% triisopropylsilane, and 2% phenol). The resulting resin was shaken for 3 hours at 700 rpm and purified via RP-HPLC.

ELISA Binding Assay: Enzyme-linked immunosorbent assay (ELISA) was carried out to test the effect of alanine substitutions within a fluorescein-labelled peptide SEQ ID NO: 1 (SEQ ID NO: 25) or flurorescein-labelled peptide SEQ ID NO: 14 (SEQ ID NO: 35) to determine residues important for binding to RHAMM. Recombinant RHAMM (100 µL, 10 µg/mL in 0.05M PBS, pH=9) was added to 96-well plates (final concentration of 1 µg/well) and incubated overnight at 4° C. Plates were washed three times with (0.05%) PBS-Tween-20 buffer (200 µL/well), followed by incubation with BSA blocking solution for 1 hour at room temperature. Fluorescein-labeled peptides (SEQ ID NO: 25 or SEQ ID NO: 35) (final concentration of 1 µg/mL) were added, washed with (0.05%) PBS-Tween-20 buffer (200 µL/well), and the absorbance was measured at 485/535 nm.

Competitive ELISA: Using competitive ELISA, the ability of alanine substituted fluorescein-labelled SEQ ID NO: 1 (SEQ ID NO: 25) or fluorescein-labelled SEQ ID NO: 14 (SEQ ID NO: 35) to displace HA and compete for RHAMM was measured. Following protein immobilization and three washes as described above, fluorescein-labeled tubulin derived peptides (final concentration of 1 µg/mL) and HA (100 µL/well, M.W. 220 kDa, 10 µg/mL in PBS, HA=1 mg/mL, 5 mg/mL and 10 mg/mL) were added to plates and incubated overnight at 4° C. The absorbance was measured at 485/535 nm after washing protocols.

Results

FIG. 10 A illustrates the affinity of twelve alanine-substituted (alanine scan) fluorescein-conjugated peptide SEQ ID NO: 1 (SEQ ID NO: 25) to RHAMM. Data show that residues 2, 4, 7-10 and 12 of SEQ ID NO: 1 may be important for proper binding to RHAMM. FIG. 10 B illustrates competitive displacement of the 12 alanine-substituted fluorescein-labelled peptides of SEQ ID NO: 1 (SEQ ID NO: 25) by HA to immobilized Rhamm-CT. Data shows that alanine substitution of SEQ ID NO: 1 at positions 2, 4, 7-10 and 12 abolishes the peptide's ability to compete with HA. Negative control (no immobilized Rhamm) was subtracted for each measurement and all data shows mean of three measurements in two independent experiments.

FIG. 17 A illustrates the affinity of 11 alanine-substituted fluorescein-conjugated peptide SEQ ID NO: 14 (SEQ ID NO: 35) to the HA-binding region of RHAMM. Data show that residue 2, 3, 5, 6, 9 and 10 of SEQ ID NO: 14 may be important for proper binding to RHAMM. FIG. 17 B illustrates competitive displacement of 11 alanine-substituted fluorescein-labelled SEQ ID NO: 14 (SEQ ID NO: 35) by HA to immobilized RHAMM-CT. Data shows that alanine substitution of SEQ ID NO: 14 at positions 2, 3, 5, 6, 9 and 10 abolishes the peptide's ability to compete with HA. Negative control (no immobilized RHAMM) was subtracted for each measurement and all data shows mean of three measurements in two independent experiments.

Example 4

Human Epithelial Ovarian Cancer Cells

Materials: Buffer solutions and media were purchased from Invitrogen, Sigma, and VWR. AlamarBlue assay kits were purchased from Invitrogen. Dimethylsulfoxide (DMSO) was purchased from Aldrich. Epithelial ovarian cancer (EOC) cells were obtained from London Regional Cancer Center following patient consents.

Proliferation Assay: The ability of one RHAMM-binding peptide (SEQ ID NO: 1) to limit the proliferation of patient derived epithelial ovarian cancer tumors and the ability of another RHAMM-binding peptide (SEQ ID NO: 3) to reduce the viability of ascites-derived human EOC cells were examined. In these assays, epithelial ovarian cancer cells (derived from ascites of patients) were plated in a 96-well plate at density 5,000 cells/well and allowed to grow for 24 hours at 37° C. and 5% CO$_2$. Peptides (1 uM and 10 uM) were added to cells on day one and proliferation was measured for 6 days. $\frac{1}{10}^{th}$ volume of Alamar Blue reagent was added directly to cells in culture medium everyday for six days. Fluorescence was read at 570/590 nm. Data were obtained from mean of two experiments. Cells treated with just DMSO (dimethylsulfoxide) and "no-cell" control samples were included in the experiment.

EOC Cell Uptake Studies: EOC cells were cultured in DMEM media+10% FBS up to 90% confluency. Then cells were seeded on 2×24-well tissue culture plates (confluency of 20,000 cells/well). Then cells were blocked with 3% BSA in DMEM+0.1% FCS for 1 hour at room temperature. For blocking experiment, antibodies (dilution 1:100, anti-IgG, goat anti-Rhamm mAb or mouse anti-CD44 mAb in DMEM+0.1% FCS media) were added and incubated at 37° C. for 1 hour. Then the resulting culture medium was aspirated, and cells were washed with DMEM+0.1% FCS at RT. Fluorescein-conjugated peptides (SEQ ID NO: 25; 50 ug/ml) were added and incubated at 37° C. for 30 minutes. Cells were washed with DMEM+0.1% FCS, then with PBS (pH=7.6), mounted using Fluoro-gel 11 containing DAPI (Electron microscopy sciences, USA) via manufacturer's protocol. Cells were photographed using Olympus FluoView FV1000 coupled IX81 Motorized Inverted System Microscope. Tiff images were analyzed using ImageJ (v1.42q) software. Each image was converted to an 8-bit format and subjected to threshold values of 20 and 255. Region of interest (ROI) were selected and mean cellular fluorescence was deduced.

Proliferation of Human Epithelial Ovarian Cancer Cells: FIG. 11 illustrates a proliferation assay of peptide SEQ ID NO: 1 in human epithelial ovarian cancer (EOC) cells. EOC cells are samples from the ascites of patients with epithelial ovarian cancer. The alamarBlue assay was used to measure the level of proliferation. Peptides of SEQ ID NO: 1 were added once on day 1 and the effect over time was measured. Data showed inhibition of proliferation in 3 of 4 patient 00 cell samples FIG. 13 illustrates the visualization of uptake of fluorescein-conjugated peptide SEQ ID NO: 1 (SEQ ID NO: 25) in ovarian tumor cells using fluorescence microscopy. As expected, uptake of the fluorescein-labelled SEQ ID NO: 1 (SEQ ID NO: 25) decreased when EOC cells were incubated with anti-RHAMM and uptake of the probe was unaffected with cells were treated with anti-IgG or anti-CD44.

Figure 12:
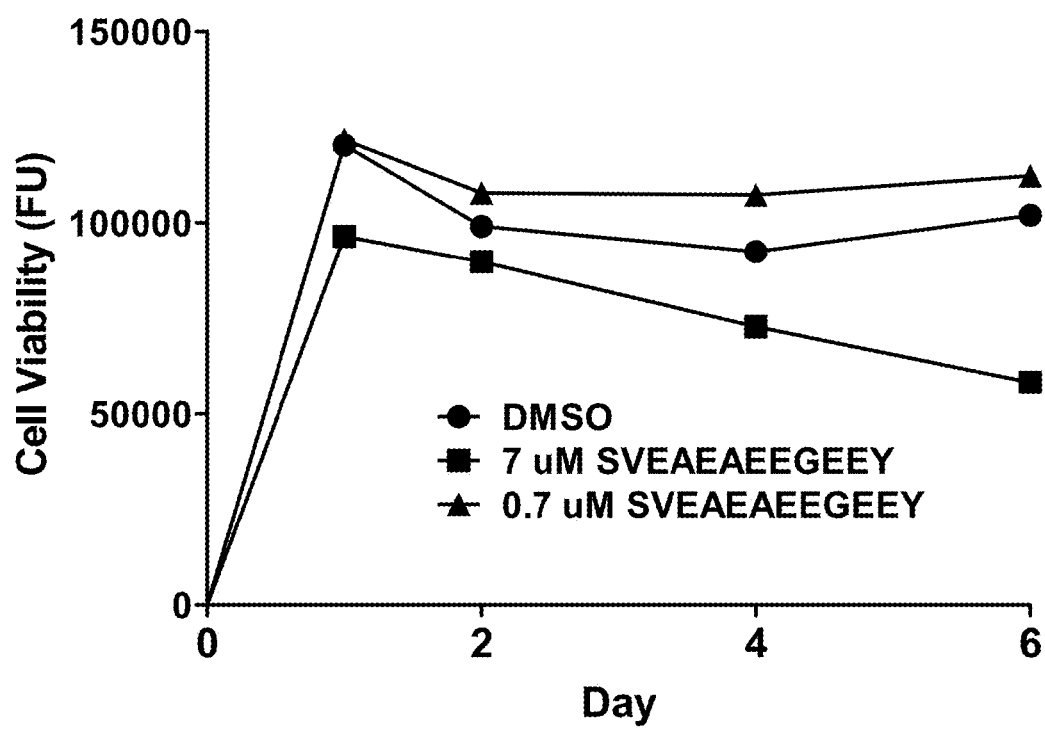
FIG. 12 is a graph illustrating reduced viability of ascites-derived human EOC cells by Rhamm-binding peptide SEQ ID NO: 3 of the present invention (p<0.05).

FIG. 12 is a graph illustrating reduced viability of ascites-derived human EOC cells by a RHAMM-binding peptide ($p<0.05$). Primary cells from patient sample EOC were seeded to a 24-well culture dish and 24 hours later treatment was initiated with the RHAMM-binding peptide SEQ ID NO: 3 (7 and 0.7 uM concentrations) or DMSO vehicle control. Re-dosing occurred everyday for up to 6 days and cell viability was assessed by fluorometry using alamarBlue™ reagent (measured in fluorescence units, FU).

Example 5

PC3mLN4 Human Prostate Cancer Lines

Materials and Methods

Cell Uptake Studies: The two hyaluronan receptors expressed by invasive/metastatic prostate tumor cells are CD44 and RHAMM. Thus, the ability of peptides of the present invention to selectively target prostate cancer cells was evaluated. In this assay, PC3mLN4 human prostate cancer cells were cultured in DMEM media+10% FBS up to 90% confluency. Then cells were seeded on glass cover slips (12×12 mm, coated with 50 ug/ml fibronectin) in 2×24-well tissue culture plates (confluency of 20,000 cells/well). Then cells were blocked with 3% BSA in DMEM+0.1% FCS for 1 hour at room temperature. For blocking experiment, antibodies (dilution 1:100, goat anti-Rhamm mAb or mouse anti-CD44 mAb in DMEM+0.1% FCS media) were added and incubated at 37° C. for 1 hour. Then the resulting culture medium was aspirated, and cells were washed with DMEM+ 0.1% FCS at RT. Fluorescein-conjugated peptides (SEQ ID NO: 29; 50 ug/ml) were added and incubated at 37° C. for 30 minutes. Cells were washed with DMEM+0.1% FCS, then with PBS (pH=7.6), mounted using Fluoro-gel 11 containing DAPI (Electron microscopy sciences, USA) via manufacturer's protocol. Cells were photographed using Olympus FluoView FV1000 coupled IX81 Motorized Inverted System Microscope. Tiff images were analyzed using ImageJ (v1.42q) software. Each image was converted to an 8-bit format and subjected to threshold values of 20 and 255. Region of interest (ROI) were selected and mean cellular fluorescence was deduced.

Peptide Uptake in PC3mLN4 Human Prostate Cancer Lines

FIG. 14 A shows the uptake of the fluorescein-conjugated peptide SEQ ID NO: 9 mimetic of HA (SEQ ID NO: 29) by PC3mLN4 human prostate cancer lines, which are aggressively invasive and metastatic. Using confocal microscopy, fluorescein-conjugated peptides were detected within tumor cells, (FIG. 14A (a), however, FITC signal decreases when RHAMM proteins are blocked with anti-RHAMM mAb (FIG. 14A (c)). This indicates that probe uptake is blocked by a specific anti-RHAMM monoclonal antibody. In addition, uptake of the fluorescein-conjugated HA mimetic does not change when cells are treated with anti-CD44 monoclonal antibody (FIG. 14A (b)). These results indicate that the HA peptide mimetic of the present invention associates with and is taken up by prostate cancer cells by a RHAMM dependent mechanism. Quantification of uptake (FIG. 14 B) showed no statistical difference in cells which receive no antibody treatment (a) and cells blocked with anti-CD44 (b). Uptake of the probe drastically decreased in cells treated with anti-RHAMM antibody (c) ($p<0.001$).

Example 6

Synthesis and Characterization of Ga-DOTA-Conjugated Peptide

Materials: Solvents were used purchased either from VWR, Fisher Scientific, or Sigma Aldrich. Rink amide MBHA resin (100-200 mesh, 0.56 mmol/g), standard Fmoc amino acids, and HBTU coupling reagents were obtained from Peptides International. 1-Bromohexanoic acid, glycine, Bromo ethylacetate and gallium (III) nitrate were purchased from Sigma Aldrich. Cyclen (1,4,7,10-tetraazacyclododecane) and $Re(CO)_5Br$ were purchased from Strem Chemicals.

Peptide Synthesis: Peptides were synthesized on rink amide MBHA resins (0.1 mmol) using standard solid phase peptide synthesis involving Fmoc deprotection and amino acid coupling cycles. Repeated Fmoc deprotection throughout the synthesis (15 and 20 minutes periods) was carried out using 20% piperidine solution in N,N-dimethylformide (DMF). All amino acid couplings were carried out using 0.05 M or higher concentration of Fmoc-protected amino acid and HBTU, 5 equivalent of N,N-diisopropylethylamine (DIPEA) in DMF at 30 and 90 minutes intervals. After each deprotection and coupling step, the resin was washed repeatedly with DMF (3×) and dichloromethane (DCM) (3×). 6-bromohexanoic acid was coupled using the same parameters. Cyclen (1,4,7,10-tetraazacyclododecane) (10 equiv.) in DMF was reacted to the end of the peptidyl chain for 3 days. Ethyl bromoacetate (3 equiv. per amine) in DMF was reacted to the secondary amine of cyclen for 24 hours to create the gallium chelator (DOTA). Purification of peptides was performed after treatment with 88% TFA using gradient solvent system consisting of $H_2O+0.1\%$ TFA (solvent A) and $CH_3CN+0.1\%$ TFA (solvent B) at a linear flow rate of 1.5 mL/min and 20 mL/min for analytical and preparative HPLC, respectively. Analytical HPLC was performed using a Grace Vydac Protein/Peptide RP-C18 column (4.6 mm×250 µm, 5 µm), and preparative HPLC was performed using a Grace Vydac protein/peptide RP-C18 column (22.0 mm×250 mm, 10 µm). Absorbance was detected at wavelengths of 220 nm and 254 nm using a Waters 2998 Photodiode Array detector. During purification, fractions were collected, lyophilized, and analyzed by ESI-MS (Waters Micromass Quattro Micro™ API).

Ga-69/71 Labelling: Gallium coordination was performed using $^{69/71}Ga(NO_3)_3$ in acetate buffer at pH 5.5 for 15 minutes. Products were isolated using C18 reverse-phase (C18 Sep-Pak©) cartridge. Products was eluted from the cartridge using 30% acetonitrile in de-ionized water with 1% trifluoroacetic acid. Resulting product was characterized using mass spectrometry, and purity was analyzed using RP-HPLC.

Synthesis and Characterization of Ga-DOTA-Conjugated Peptide $^{67/71}$Ga-DOTA-conjugated peptide SEQ ID NO: 1 was synthesized and characterized as a possible non-radioactive surrogate for $^{68}$Ga-coordinated radiotracer for PET imaging. FIG. 15 A describes the gallium labelling of DOTA-conjugated peptide. FIG. 15 B illustrates RP-HPLC chromatogram of purified gallium coordinated peptide at 9.73 minutes. FIG. 15 C illustrates an ESI mass spectrum of the compound of FIG. 15 A (observed: 936.7 $[M+2H]^{2+}$, calculated: 934.87 $[M+2H]^{2+}$).

Example 7

Synthesis and Characterization of $Re(CO)_3^+$-Coordinated Peptide

Materials: Solvents were used purchased either from VWR, Fisher Scientific, or Sigma Aldrich. Rink amide MBHA resin (100-200 mesh, 0.56 mmol/g), standard Fmoc amino acids, and HBTU coupling reagents were obtained from Peptides International. Glycine, sodium cyanoborohydride and 3-Pyridinecarboxaldehyde were purchased from Sigma Aldrich. $Re(CO)_5Br$ was purchased from Strem Chemicals $Re(CO)_3^+$ Chelator Synthesis ([bis(pyridin-2-lymethyl) amino]acetic acid): To a solution of glycine (0.602 g, 8.02 mmol) in 10% acetic acid (20 mL), 3-Pyridinecarboxaldehyde (4.28 g, 0.02 mol) was added in excess. After 1 hour stirring at room temperature, sodium cyanoborohydride (1.01 g, 0.016 mol) was added and the resulting reaction mixture was stirred for 24 hours. The resulting mixture was extracted with chloroform (3×40 mL), dried with $MgSO_4$, and volatiles were evaporated to yield a yellow oil. Crude product was purified using silica chromatography (90% chloroform: 10% methanol) (1.67 g, 81% yield)

Peptide Synthesis: Peptides were synthesized on rink amide MBHA resins (0.1 mmol) using standard solid phase peptide synthesis involving Fmoc deprotection and amino acid coupling cycles. Repeated Fmoc deprotection throughout the synthesis (15 and 20 minutes periods) was carried out using 20% piperidine solution in N,N-dimethylformide (DMF). All amino acid couplings were carried out using 0.05 M or higher concentration of Fmoc-protected amino acid and HBTU, 5 equivalent of N,N-diisopropylethylamine (DIPEA) in DMF at 30 and 90 minutes intervals. After each deprotection and coupling step, the resin was washed repeatedly with DMF (3×) and dichloromethane (DCM) (3×). Fmoc-aminohexanoic acid and ([bis(pyridin-2-Iymethyl) amino]acetic acid were coupled using methods described above. Rhenium coordination was carried out using excess $[Re(CO)_3Br_3](NEt_4)_2$. Cleavage from solid support was carried out using 88% trifluoroacetic acid.

Purification of peptides was performed using gradient solvent system consisting of $H_2O+0.1\%$ TFA (solvent A) and $CH_3CN+0.1\%$ TFA (solvent B) at a linear flow rate of 1.5 mL/min and 20 mL/min for analytical and preparative HPLC, respectively. Analytical HPLC was performed using a Grace Vydac Protein/Peptide RP-C18 column (4.6 mm×250 µm, 5 µm), and preparative HPLC was performed using a Grace Vydac protein/peptide RP-C18 column (22.0 mm×250 mm, 10 µm). Absorbance was detected at wavelengths of 220 nm and 254 nm using a Waters 2998 Photodiode Array detector. During purification, fractions were collected, lyophilized, and analyzed by ESI-MS (Waters Micromass Quattro Micro™ API).

Figure 16:
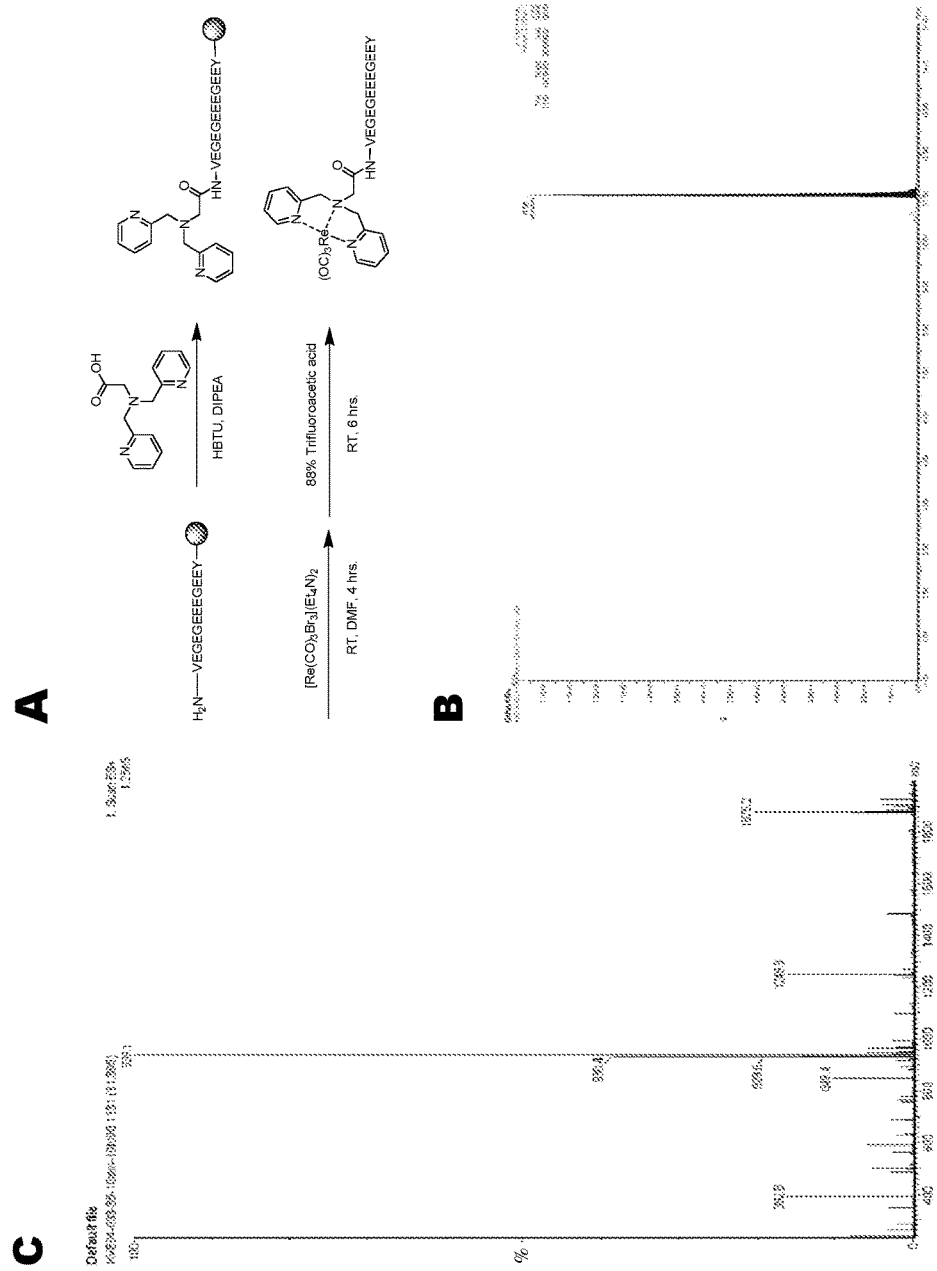
FIG. 16 A illustrates the synthesis of $Re(CO)_3^+$-coordinated SEQ ID NO: 1 peptide.

Re(CO)$_3$$^+$-coordinated peptide SEQ ID NO: 1 was synthesized and characterized as a possible non-radioactive surrogate for $^{99}$Tc(CO)$_3$$^+$ coordinated radiotracer for SPECT imaging. FIG. 16 A describes the synthesis of Re(CO)$_3$$^+$-coordinated peptide SEQ ID NO: 1 and FIG. 16 B illustrates RP-HPLC chromatogram of purified rhenium coordinated peptide at 11.06 minutes. FIG. 16 C illustrates an ESI mass spectrum of the rhenium coordinated peptide (observed: 939.1 [M+2H]$^{2+}$, calculated: 940.2 [M+2H]$^{2+}$).

NON-PATENT REFERENCES

1. Edward, M., et al., Tumour regulation of fibroblast hyaluronan expression: a mechanism to facilitate tumour growth and invasion. Carcinogenesis, 2005. 26(7): p. 1215-23.
2. Tammi, M. I., A J. Day, and E. A. Turley, Hyaluronan and homeostasis: a balancing act. J Biol Chem, 2002. 277(7): p. 4581-4.
3. Gotte, M. and G. W. Yip, Heparanase, hyaluronan, and CD44 in cancers: a breast carcinoma perspective. Cancer Res, 2006. 66(21): p. 10233-7.
4. Guo, Yan-Ting et al. International Journal of Peptide Research and Therapeutics 11:159 (2005).
5. Aniel A. et al. Rapid Comm Mass Spectr. 21:2237 (2007).
6. J. Am. Chem. Assoc. 65:2149 (1964).
7. J. Amer. Chem. Soc. 85:2149 (1963).
8. Int. J. Peptide Protein Res. 35:161-214 (1990).
9. Methods of Organic Chemistry, E. Wansch (Ed.) Vol. 15, pts. I and II, Thieme, Stuttgart (1987).
10. Sambrook et al, Molecular Cloning: A Laboratory Manual (2nd ed.), Vols. 1-3, Cold Spring Harbor Laboratory, (1989).
11. Current Protocols in Molecular Biology, F. Ausubel et al., ed. Greene Publishing and Wiley-Interscience, New York (1987).
12. Larkin, M. A.; Blackshields, G.; Brown, N. P.; Chenna, R.; McGettigan, P. A.; McWilliam, H.; Valentin, F.; Wallace, I. M.; Wilm, A.; Lopez, R.; Thompson, J. D.; Gibson, T. J.; Higgins, D. G. (2007) Clustal W and Clustal X version 2.0. Bioinformatics, 23(21), 2947-2948.
13. Tolg, C.; Hamilton, S. J.; Morningstar, L.; Zhang, J.; Esguerra, K. V.; Telmer, P. G.; Luyt, L. G.; Harrison, R.; McCarthy, J. B.; Turley, E. A. (2010) RHAMM promotes interphase microtubule instability and mitotic spindle integrity trough MEK1/ERK1, 2 activity. J Biol. Chem., 285, 26461-26474.
14. Maxwell, C. A.; Keats, J. J.; Crainie, M.; Sun, X.; Yen, T. Shibuya, E.; Hendzel, M. Chan, G.; and Pilarski, L. M. (2003) RHAMM is a centrosomal protein that interacts with dynein and maintains spindle pole stability. Mol. Biol. Cell., 14, 2262-2276.
15. Chan, W. C.; White, P. D. (2000) Fmoc Solid Phase Peptide Synthesis; Chan, W. C., White, P. D. Eds.; Oxford university Press: New York, pp 41-76.
16. Kaiser, E.; Colescott, R. L.; Bossinger, C. D.; Cook, P. I. (1970) Color test for detection of free terminal amino groups in the solid phase synthesis of peptides. Biochem. 34, 595-598.
17. Zhang, L; Furst, E M; Kiick, K L. (2006) Manipulation of hydrogel assembly and growth factor delivery via the use of peptide-polysaccharide interactions. J Control Release, 114, 130-42.
18. Cross, D.; Dominguez, J.; Maccioni, R. B. (1991) MAP-1 AND MAP-2 binding sites at the C-terminus of beta-tubulin. Studies with synthetic tubulin peptides. *Biochemistry*, 30(17), 4362-4366.

We claim:

1. A purified receptor for hyaluronic acid mediated motility (RHAMM)-binding peptide, wherein said RHAMM-binding peptide consists of an about 12 to about 14 amino acid long peptide containing SEQ ID NO: 12 or a variant thereof having a single conservative amino acid substitution.

2. The RHAMM-biding peptide of claim 1, wherein said RHAMM-binding peptide consists of SEQ ID NO: 12.

3. The RHAMM-binding peptide of claim 1, wherein said RHAMM-binding peptide is conjugated to a detectable label.

4. The RHAMM-binding peptide of claim 3, wherein the detectable label is selected from biotin-based labels, magnetic labels, radioactive labels, fluorescent labels, electron-dense reagents, enzymes, digoxigenin, and haptens.

5. The RHAMM-binding peptide of claim 4, wherein said RHAMM-binding peptide is conjugated to fluorescein.

6. The RHAMM-binding peptide of claim 5, wherein said RHAMM-binding peptide comprises SEQ ID NO: 33.

7. The RHAMM-binding peptide of claim 3, wherein said RHAMM-binding peptide is conjugated to a Ga-DOTA label or to a $Re(CO)_3^+$ label.

8. The RHAMM-binding peptide of claim 1, wherein said RHAMM-binding peptide is conjugated to a cytotoxic molecule or radioactive molecule.

9. A pharmaceutical composition comprising an effective amount of the peptide of claim 1 and a pharmaceutically acceptable carrier.

10. The pharmaceutical composition of claim 9, wherein the peptide is provided in a liposome, immunoliposome, or lipid formulation.

11. A method for blocking a RHAMM/hyaluronan interaction, comprising contacting cells with an effective amount of the RHAMM-binding peptide of claim 1.

12. A method of imaging RHAMM expression in cells, tissues, or organs, comprising contacting the cells, tissues, or organs with the RHAMM-binding peptide of claim 3 and applying an imaging technique for detecting the label in the cells, tissues or organs, wherein detection of the label in the cells, tissues, or organs indicates the expression of RHAMM in the cells, tissues, or organs.

13. The method of claim 12, wherein the cells, tissues, or organs are imaged in vivo.

14. The method of claim 12, wherein the cells, tissues, or organs are imaged ex vivo.

15. The method of claim 12, wherein the detectable label comprises a radionucleotide and the technique is selected from the group consisting of SPECT, CT, and PET.

16. The method of claim 13, wherein the method comprises:
delivering the RHAMM-binding peptide to the cells, tissues, or organs by intravenous, intramuscular, subcutaneous, intraperitoneal, oral, or intranasal administration to a subject; or
implanting the RHAMM-binding peptide into a tissue or organ of a subject.

17. The method of claim 12, wherein the cells, tissues, or organs are human cells, tissues, or organs.

18. The method of claim 12, wherein the method further comprises: (a) obtaining a tumor tissue sample from the subject, wherein the subject is a cancer patient; (b) contacting said sample with the RHAMM-binding peptide; (c) applying the imaging technique for detecting the label in the sample; and (d) determining a prognosis for the patient, wherein the prognosis predicts a probability of aggressiveness or metastasis of the cancer in the patient, and wherein detection of RHAMM expression in the sample indicates a poor prognosis.

19. The method of claim 18, wherein the method further comprises prescribing a course of treatment for the patient based on the prognosis.

20. The method of claim 12, wherein the method further comprises: (a) obtaining a tumor tissue sample from the subject; (b) contacting said sample with the RHAMM-binding peptide; and (c) applying the imaging technique for detecting the label in the sample; wherein detection of RHAMM expression in the sample indicates a positive diagnosis of the disorder or condition.

21. The method of claim 20, wherein the disorder or condition is cancer.

22. The RHAMM-binding peptide of claim 1, wherein the peptide is PEGylated.

23. The RHAMM-binding peptide of claim 1, wherein the peptide comprises one or more D-amino acids.

24. The RHAMM-binding peptide of claim 1, wherein the peptide is acetylated.

25. The RHAMM-binding peptide of claim 1, wherein the peptide is amidated.

* * * * *